(12) United States Patent
Barski et al.

(10) Patent No.: US 6,630,324 B1
(45) Date of Patent: Oct. 7, 2003

(54) ALDEHYDE REDUCTASE BIDIRECTIONAL PROMOTER AND ITS USE

(75) Inventors: Oleg A. Barski, Houston, TX (US); Estuardo C. Aguilar-Cordova, Newton, MA (US); Kurt M. Bohren, Pearland, TX (US); Kenneth H. Gabbay, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 562 days.

(21) Appl. No.: 09/626,002

(22) Filed: Jul. 26, 2000

Related U.S. Application Data

(60) Provisional application No. 60/146,266, filed on Jul. 29, 1999.

(51) Int. Cl.$^7$ .................. C12N 15/09; C12N 15/00; C12N 5/10; C07H 21/04
(52) U.S. Cl. ................ 435/69.1; 435/320.1; 435/375; 536/24.1
(58) Field of Search ................ 435/320.1, 374, 435/69.1, 375; 536/24.1

(56) References Cited

U.S. PATENT DOCUMENTS 5,627,046 A * 5/1997 Falcone et al. ............ 435/69.1
5,654,168 A * 8/1997 Bujard et al. ............. 435/69.1

OTHER PUBLICATIONS

Linton et al. Dual bidirectional promoters at the mouse dhfr locus: cloning and characterization of two mRNA classes of the divergently transcribed Rep–1 gene. Molecular and Cellular Biology. 1989, vol. 9, pp. 3058–3072.*
Anderson. Human gene therapy. Nature. 1998. vol. 392, pp. 25–30.*
Branch. A good antisense molecule is hard to find. TIBS. 1998. vol. 23, pp. 45–50.*
A–Mohammadi S. et al., *Efficient transgene regulation from a single tetracycline–controlled positive feedback regulatory system*; Gene Therapy, 1998, pp. 76–84, vol. 5, Stockton Press.
Strathdee C.A., et al., *Efficient control of tetracycline–responsive gene expression from an autoregulated bi–directional expression vector*, Gene, 1999, pp. 21–29, vol. 229, Elsevier Science B.V.
Huang W., et al., *TATA elements direct bi–directional transcription by RNA polymerases II and III*, Nucleic Acids Research, 1996, pp. 1158–1163, vol. 24, No. 6, Oxford University Press.
Chatterjee–Kishore M., et al., *Different requirements for signal transducer & activator of transcription 1α & interferon regulatory factor 1 in the regulation of low molecular mass polypeptide 2 & transporter associated with antigen processing 1 gene expression*, The Journal of Biological Science, Jun. 26, 1998, pp. 16177–16183, vol. 273, No. 26.
Xu C.F., et al., *Complex regulation of the BRCA1 gene*, The Journal of Biological Science, Aug. 22, 1997, pp. 20994–20997, vol. 272, No. 34, The American Society for Biochemistry & Molecular Biology, Inc.
Johnson P., et al., *Limited bidirectional activity of two housekeeping gene promoters: human HPRT & PGK*, Gene, 1990, pp. 207–213, vol. 88, Elsevier.
Koller E., et al. *The promoter of the chicken α2(VI) collagen gene has features characteristic of house–keeping genes & of proto–oncogenes*, Nucleic Acids Research, 1991, pp. 485–491, vol. 19, No. 3, Oxford Univ. Press.

* cited by examiner

Primary Examiner—James Ketter
Assistant Examiner—Lisa Gansheroff
(74) Attorney, Agent, or Firm—Fulbright & Jaworski, L.L.P.

(57) ABSTRACT

The invention relates to an aldehyde reductase bidirectional promoter which promotes transcription of two different sequences linked in opposite orientations. Vectors containing said promoter and methods of using said promoter are described.

34 Claims, 12 Drawing Sheets

```
liver     AGCCAGAAATGTGAAGTGCTAGCTGAAGGATGAGCAGCTAGCCA      1
                   10         20         30        40 adrenal ...GCAGAACTGAGCCCCAGGCCCACAGTACCCTATTCACGCTCTGTGCTTG   110
                80         90        100        110 liver    GGGGCAATGGCGGCTTCCTGTGTTCT..........              1132
         ||||||||||||||||||||||||||
adrenal  GGGGCAATGGCGGCTTCCTGTGTTCT..........              1203
              130        140        150
```

FIG. 2

```
-420  TAAAACCATG TTTATTAAGT GTTAAGCACA GTGCCTGGCA CATAACGTGC TGGGCG
-360  CTATGGTCCA GACAGGGGGA CCAGGCACTT TCCAGCGCCT GGATCTGCAG ACGCGA
-300  TTCTGTATTC TGGCCAATCT TGGTGTTGCA GCTGCTCTCT GGGCCTCAGT TTGCTT
-240  TAAATGTAAC GGGGCCAACT TAGGTGAACT TTGGGAATCC AGCCAACCTG ACTTTA
-180  GAGTATGGAG CCACGGATGG CATTGTGAAT CCGGAGGGCC GACACCAGAA GAACCT
-120  CGTGGCATCT GCTACCTTAC TTCCCCCGGA AAAGCGCCTG CGGCGGGCGCC TAGGCG
 -60  GTGCAATGTG GGCCAGCAAA AGGCGAGGCT GGCCCCGCCC CTTGCACCGC CCACGT
  +1  AGCGCCACCT GCCTCATTGT GCCCAGGAGT TCTCCAAACC CGGGCTGCGG AGTGAG
 +60  CAAGTTCCGG CCAGTTCGAC CTCGAGGATC
```

FIG. 7

ALDEHYDE REDUCTASE BIDIRECTIONAL PROMOTER AND ITS USE

This application claims priority to U.S. Provisional Patent Application Serial No. 60/146,266 filed Jul. 29, 1999.

The work herein was supported by grants from the United States Government. The United States Government may have certain rights in the invention.

FIELD OF THE INVENTION

This invention relates to the use of a single bidirectional promoter from the aldehyde reductase gene to regulate expression of two separate genes linked in opposite orientations. More particularly it relates to the use of said bidirectional promoter to regulate expression of two separate genes for applications which require production of two separate gene products in the same cell, including applications which require approximately equimolar amounts of said two separate gene products.

BACKGROUND OF THE INVENTION

Aldehyde reductase is a member of the aldo-keto reductase superfamily which consists of more than nearly 80 known enzymes and proteins. In addition, genome sequencing projects have identified approximately 150 potential aldo-keto reductase genes, many of which have no assigned function. It is an enzyme which protects cells from environmental and nutritional toxins and carcinogens by detoxification of reactive aldehydes (Bachur, 1976; Feather et al., 1995; Suzuki et al., 1998). It reduces a wide variety of aldehydes to their corresponding alcohols using NADPH as a cofactor. The crystal structures of several members of the superfamily show an $\alpha/\beta$ barrel structure with an active site located at the C-terminal end of the barrel (Rondeau et al., 1992; Wilson et al., 1992; Harrison et al., 1994; el-Kabbani et al., 1995; Bennett et al., 1996; Wilson et al., 1995). The catalytic residues are highly conserved in the family and include a Tyr-Lys-Asp catalytic triad (Bohren et al., 1994; Barski et al., 1995; Bruce et al., 1994). The enzymatic properties of this enzyme have been extensively studied, (Barski et al., 1996a; Barski et al., 1996b), and it is ubiquitously distributed in tissues with the highest amounts found in kidney, liver and thyroid (Gabbay et al., 1974; Wirth et al., 1985; Barski et al., 1999). The enzyme is found in all eukaryotes from yeast to mammals. Based on their wide substrate specificity, aldo-keto reductases are thought to be involved in general detoxification of reactive aldehydes. More specific roles for aldehyde reductase were suggested in glucuronate metabolism (Mano et al., 1961), in neurotransmitter metabolism (products of monoamine oxidase) (Tipton et al., 1977; Turner et al., 1974), and in steroid metabolism particularly with respect to isocorticosteroids which are the best-known substrates for this enzyme (Wermuth et al., 1983).

Several regulatory pathways have been identified for the expression of various members of the aldo-keto reductase superfamily. For instance, aldose reductase expression is induced by hypertonicity in all tissues (Bagnasco et al., 1987); and chlordecone reductase is induced in the liver by chlordecone (Molowa et al., 1986a; Molowa et al., 1986b). Comparison of the human aldehyde reductase gene structure to other determined aldo-keto reductase genes (Graham et al., 1991; Wang et al., 1993; Lou et al., 1994; Qin et al., 1994; Khanna et al., 1995) suggests that it is more distantly related to these genes than they are among themselves. Previous studies have not addressed the mechanism of regulation of the aldehyde reductase gene. The present invention identifies alternative splicing of a single primary transcript and the single most important active promoter element. More importantly, the present invention describes the bidirectional function of the promoter of aldehyde reductase and its use to produce two proteins within the same cell.

Expression of two proteins at a time is becoming an increasingly important practical task for research and biotechnology. In biomedicine, it is often necessary to introduce two proteins into the patient's cells to achieve a therapeutic effect. Examples include two polypeptide chains that assemble into active protein, e.g. light and heavy chain of antibodies, IL-12, etc. New systems for expression of two genes in equal amounts would therefore be useful for production of heterodimeric proteins and for simultaneous expression of selectable or marker genes and a gene of interest.

Examples of other promoters possessing bidirectional activity have been described, yet many of these promoters exhibit significant differences when comparing the transcriptional levels generated by the alternate orientations of the promoter (e.g. Xu et al., 1997; Johnson and Friedmann, 1990 and U.S. Pat. Nos. 5,258,294; 5,338,679; and 5,368,855). Furthermore, there are examples in the art of promoters concluded to be bidirectional (e.g. Koller et al., 1991; Linton et al., 1989); however, in these examples assays for potential bidirectional promoter activity utilized a reporter gene linked to opposite orientations of the promoter on separate constructs.

Other art exists which utilizes the tetracycline (Tet) operon in which operator sequences, regulated by a recombinant Tet repressor, are flanked by two minimal promoters which drive transcription of two separate genes (U.S. Pat. Nos. 5,589,362; 5,654,168; 5,789,156; 5,814,618; 5,866,755; 5,891,718; Clontech). In the Tet system, the same promoter is cloned twice in opposite orientations and drives transcription of separate genes. However, the likelihood of reduced stability of nucleotide sequences increases upon duplication of sequences. Furthermore, at least one operator sequence is present between the two promoters for regulation by the Tet repressor protein. Finally, the Tet system requires the use of specially prepared cell lines which express the regulator protein.

Alternative methods to produce two proteins within the same cell employ variations of constructs which contain an Internal Ribosome Entry Site (IRES) (WO 97/20935; WO 98/11241; WO 98/12338; WO 98/37189; WO 98/49334; WO 98/54342; WO 98/55636; WO 99/24596; WO 99/25817; for specific examples see e.g. U.S. Pat. Nos 5,665,567 or 5,770,428; Clontech), which directs cap-independent translation (Jang et al., 1990; Belsham and Sonenberg, 1996). As a result, one bicistronic RNA is transcribed and two separate proteins are translated from a single transcript. However, this method has an inherent drawback that translation from an IRES is often reduced compared to the initial translation start site (Jang et al., 1989). Another alternative is to use two promoters, one for each gene. However, this may lead to construct instability or to grossly different levels of transcription (Ju et al., 1980; Junker et al., 1995). Using a single bidirectional promoter provides a potential for expression of two genes in equivalent amounts and may circumvent drawbacks of current alternatives.

SUMMARY OF THE INVENTION

An embodiment of the present invention is a DNA sequence and fragments and derivative thereof which function as bidirectional promoters. An additional embodiment is said DNA sequence selected from the group consisting of SEQ ID NO: 19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31. In a specific embodiment, said promoter has the characteristic of promoting transcription of two separate nucleotide sequences wherein one of such nucleotide sequences is operatively linked to the 5' end of said promoter sequence and is transcribed 5' to 3' in the direction opposite from the 5' to 3' direction of said promoter sequence and the other of such nucleotide sequences is operatively linked to the 3' end of said promoter sequence and is transcribed 5' to 3' in the same direction as the 5' to 3' direction of said promoter sequence. In a further embodiment, said promoter promotes transcription of the said two nucleotide sequences in approximately equimolar amounts. In an additional embodiment said promoter is the aldehyde reductase promoter.

In another embodiment of the present invention there is a recombinant DNA vector comprising the promoter sequence selected from the group consisting of SEQ ID NO: 19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31 or fragments and derivatives thereof, wherein said fragments and derivatives function as a bidirectional promoter; a first DNA sequence encoding a gene operatively linked to the 5' end of the promoter sequence wherein when said first DNA sequence is transcribed it is transcribed 5' to 3' in the direction opposite from the 5' to 3' direction of the promoter sequence; and a second DNA sequence encoding a gene operatively linked to the 3' end of the promoter sequence wherein when said second DNA sequence is transcribed it is transcribed 5' to 3' in the same direction as the 5' to 3' direction of the promoter sequence. In a specific embodiment, said vector also contains a poly A+ polyadenylation sequence operatively linked to the 3' end of at least one of said first or second nucleotide sequences. In a further embodiment, said nucleotide sequences are nonidentical. In a specific embodiment, at least one said nucleotide sequence of said vector encodes a reporter sequence. In a specific embodiment said reporter sequence is selected from the group consisting of ampicillin, neomycin, kanamycin, luciferase, β-galactosidase, β-glucuronidase, chloramphenicol acetyl transferase (CAT), blue fluorescent protein (BFP), green fluorescent protein (GFP), or placental alkaline phosphatase. In further embodiments, said nucleotide sequences encode heavy and light chains of an antibody, subunits of an interleukin, subunits of a growth hormone receptor, a subunit of a homodimer, or subunits of a heteterodimer. In an additional embodiment we claim the method of preparing said antibody, interleukin, growth hormone receptor, homodimer, and heterodimer comprising expression of said nucleotide sequences and recovering the formed product. A specific embodiment of the present invention is the vector wherein one DNA sequence encodes a therapeutic nucleotide sequence and the other DNA sequence encodes a suicide gene.

An additional embodiment of the present invention is said vector wherein at least one nucleotide sequence encodes an RNA; said RNA being the final product of said nucleotide sequence and containing functional characteristics. In another embodiment we claim the method of preparing a recombinant ribonucleoprotein encoded for by the DNA sequences of the recombinant DNA vector comprising the expression of said DNA sequences and recovery of the recombinant functional ribonucleoprotein. In a further embodiment we claim the method of preparing recombinant RNAs encoded for by the sequences of said recombinant DNA vector comprising expression of said DNA sequences and recovery of functional RNAs. In specific embodiments said functional RNA can be a snRNA, a snoRNA, a scRNA, the telomerase RNA, an antisense RNA, or the XIST RNA.

An additional embodiment is the recombinant DNA vector comprising the promoter sequence selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31 or fragments and derivatives thereof when said fragments and derivatives function as a bidirectional promoter; a first polylinker site into which a first DNA sequence is operatively linked to the 5' end of the promoter sequence wherein when said first DNA sequence is transcribed it is transcribed 5' to 3' in the direction opposite from the 5' to 3' direction of the promoter sequence; and a second polylinker site into which a second DNA sequence encoding a gene operatively linked to the 3' end of the promoter sequence wherein when said second DNA sequence is transcribed it is transcribed 5' to 3' in the same direction as the 5' to 3' direction of the promoter sequence.

An additional embodiment is said vector further comprising a poly A+ polyadenylation sequence operatively linked to the 3' end of at least one of said first or second nucleotide sequences.

In a specific embodiment there is a recombinant DNA vector comprising a cassette, wherein said cassette comprises one DNA sequence which encodes a suicide nucleic acid sequence and the other DNA sequence which encodes an immortalization nucleic acid sequence. In a specific embodiment the suicide nucleic acid sequence is thymidine kinase (TK). In another specific embodiment the immortalization nucleic acid sequence is selected from the group consisting of T-antigen, telomerase catalytic protein subunit and myc.

In another specific embodiment there is a method to initiate proliferation of a cell comprising the step of introducing the vector comprising a cassette, wherein said cassette comprises one DNA sequence which encodes a suicide nucleic acid sequence and the other DNA sequence which encodes an immortalization nucleic acid sequence, into said cell under conditions wherein activation of the bidirectional promoter to transcribe said immortalization nucleic acid sequence in said cell initiates proliferation of said cell. In another specific embodiment the vector further comprises excision sites flanking said cassette, wherein said excision sites are selected from the group consisting of lox, FLP recognition target sites, restriction endonuclease sites, and transposon sequences.

In an additional specific embodiment there is a method to initiate proliferation of a cell comprising the step of introducing a vector comprising a cassette, wherein said cassette comprises one DNA sequence which encodes a suicide nucleic acid sequence and the other DNA sequence which encodes an immortalization nucleic acid sequence, wherein the vector further comprises excision sites flanking said cassette, wherein said excision sites are selected from the group consisting of lox, FLP recognition target sites, restriction endonuclease sites, and transposon sequences, into said cell under conditions wherein activation of the bidirectional promoter to transcribe said immortalization nucleic acid sequence in said cell initiates proliferation of said cell. In a specific embodiment the introduction step further comprises integration of said excision sites and said cassette into a provirus of said cell. In an additional embodiment the method further comprises excising said immortalization nucleic acid sequence from said provirus through said excision sites. In a further specific embodiment the method further comprises destroying a cell which has failed to excise said immortalization nucleic acid sequence. In an additional specific embodiment the cell is a primary cell. In another specific embodiment the primary cell is selected from the group consisting of insulin-producing beta cell and liver cell.

DESCRIPTION OF THE DRAWINGS

FIG. 2 shows the alternative aldehyde reductase cDNAs. Sequence comparison of the 5' ends of aldehyde reductase cDNAs cloned from liver (SEQ ID NO:1) and from adrenal gland (SEQ ID NO:2) is presented. The initiation codons, ATG, are underlined.

FIG. 7 shows sequence of the aldehyde reductase gene promoter region (−420 to +90) (SEQ ID NO:3). The nucleotide position +1 corresponds to the transcription start site as determined by primer extension. Possible binding sites of several transcription factors of interest are shown underneath the sequence.

DESCRIPTION OF THE INVENTION

The term "5' to 3'" as used herein is defined as the orientation of DNA in which the succession of the nucleotides comprising the sugar-phosphate links of the DNA molecule are oriented beginning with the fifth carbon of the 2-deoxyribose of the first nucleotide and ending with the third carbon of the 2-deoxyribose of the last nucleotide. It furthermore refers to the direction of transcription which occurs in said succession. A skilled artisan is aware that although synthesis of RNA (growth of an RNA chain) is in the 5' to 3' direction, the RNA polymerase core moves along the DNA strand in the 3' to 5' direction because the template strand is antiparallel to the newly synthesized RNA strand.

The term "approximately equimolar" as used herein is defined as having similar molar levels of two RNAs, two proteins, or one RNA and one protein. Similar molar levels as used herein is defined as the levels of two RNAs, two proteins, or one RNA and one protein having a discrepancy no greater than a 60:40 ratio.

Figure 1:
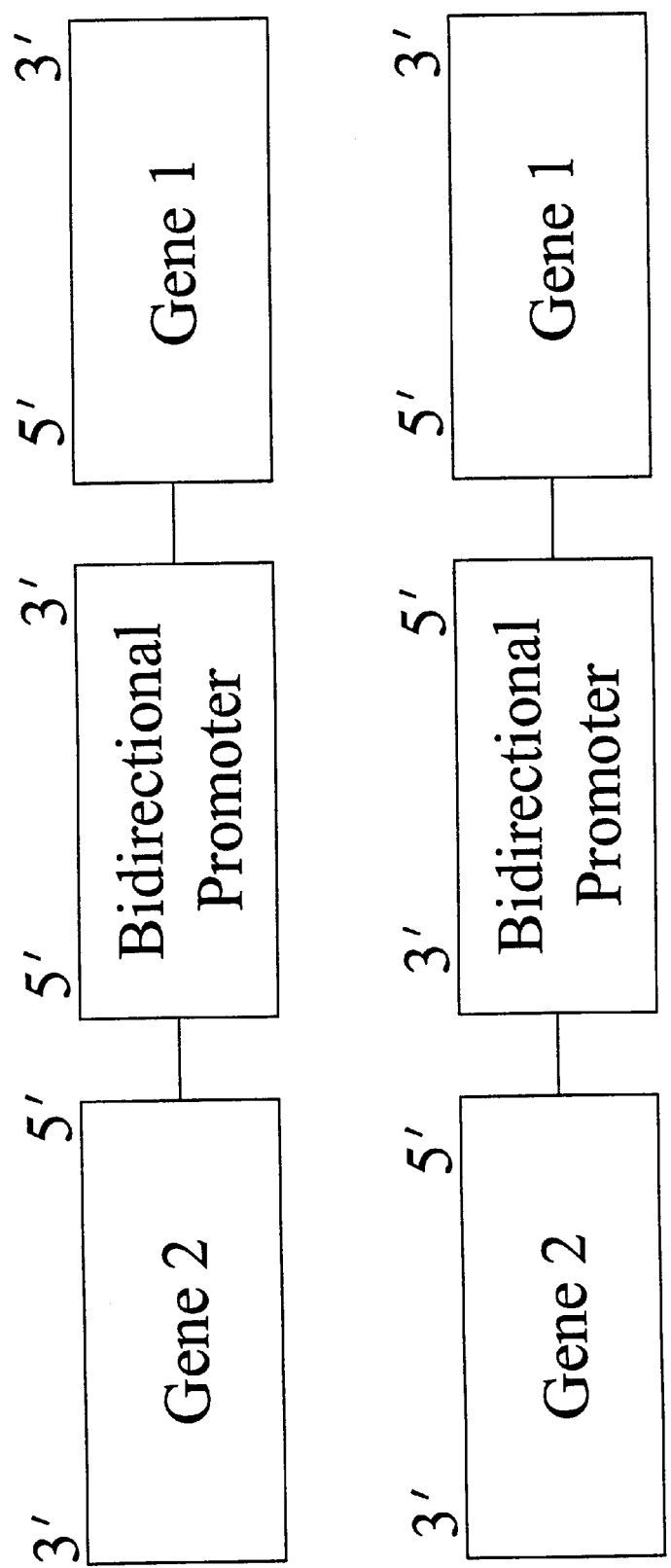
FIG. 1 depicts alternative orientations of the bidirectional promoter and the associated nucleotide sequences as they pertain to the invention.

The term "bidirectional promoter" as used herein is defined as a promoter which directs transcription of specific nucleotide sequences in opposite orientations. That is, it directs transcription of a specific nucleotide sequence which lies 5' to 3' in the same 5' to 3' direction as said promoter and it directs transcription of another specific nucleotide sequence which lies 5' to 3' in a direction opposite from the 5' to 3' direction of said promoter. The nucleotide sequences are in fixed positions relative to the promoter sequence with the 5' ends of said nucleotide sequences always positioned most proximal to the promoter. However, the orientation of said promoter can be reversed relative to its position between said diverging nucleotide sequences and still allow promoter activity. For example see FIG. 1.

The term "blunt-cutter restriction enzyme site" as used herein is defined as a restriction enzyme site at which said enzyme cleaves one phosphodiester bond of each DNA strand between the same two specific hydrogen-bonded base pairs. Said cleavage produces DNA fragments with ends which contain no single stranded protrusion. Said sites may be of any size or form, including methylated form, and examples include SmaI, EcoRV, or XmnI.

The term "DNA" as used herein is defined as deoxyribonucleic acid.

The term "excision site" as used herein is defined as a site in a nucleic acid sequence which is utilized to permit removal of a specific sequence. In a specific embodiment it is a recombination site. Examples of excision sites include the lox sites, such as loxP used with the Cre-lox system, Flp recombinase target sites, transposon sequences (permitting that a transposase is provided by means well known in the art), and restriction endonuclease sites (such as rare cutter restriction endonuclease sites which are not present in the human genome).

The term "final product" as used herein is defined as an end product, which may also be called a gene product, which may be an expressed nucleic acid that is an RNA or it may be an amino acid sequence (such as a protein or peptide) translated from an intermediate ribonucleic acid species. In a specific embodiment the intermediary RNA molecule, such as an mRNA, is not considered herein a final product of the expressed nucleic acid. In a specific embodiment the final product which is an RNA is not translated to an amino acid but performs its function as an RNA.

The term "fragments and derivatives thereof" refers to alterations of specific nucleotide sequence including mutations, chemical modifications, deletions, or additions which still allow the promoter to function as a bidirectional promoter as described herein. Such changes could enhance or decrease the ability of the promoter. Furthermore, subregions of said promoter could be utilized as a bidirectional promoter and could furthermore contain mutations, chemical modifications, deletions, or additions which still allow said subregion of said promoter to function as a bidirectional promoter as described herein. A skilled artisan is aware how to make such alterations or chemical modifications through standard methods texts well known in the art. Examples of such texts include Sambrook et al. (1989) and Ausubel et al. (1994). One skilled in the art has provided herein methods in the Examples how to test these fragments and derivatives for bidirectional promoter activity.

The term "functional RNA" as used herein is defined as an RNA which possesses some operational activity and does not refer to the RNA molecule merely as a template for protein production; said RNA is the final product of said nucleotide sequence. Such activity could include catalysis of a reaction, such as a ribozyme, or as part of a ribonucleoprotein to generate catalysis of some biological function. Examples of such functional RNAs include those found in snRNPs, scRNPs, snoRNPs, the XIST RNA, an antisense RNA, and the telomerase RNA.

The term "immortalization nucleic acid sequence" as used herein is a nucleic acid sequence which permits proliferation of a cell. In a specific embodiment the immortalization nucleic acid sequence is a T-antigen. In an additional specific embodiment the T-antigen is Simian Virus 40 T-antigen, although others known in the art may be utilized. In other specific embodiments the immortalization nucleic acid sequence is a telomerase catalytic protein subunit or myc.

The term "non blunt-cutter restriction enzyme site" as used herein is defined as a restriction enzyme site at which said enzyme cleaves one phosphodiester bond of each DNA strand between two different specific hydrogen-bonded base pairs. Said cleavage produces DNA fragments with ends which contain either a 5' or 3' single stranded protrusion. Said sites may be of any size or form, including methylated form, and examples include EcoRI, Sac I, or Sal I.

The term "polylinker site" as used herein is defined as a site containing at least one restriction enzyme site for the purpose of inserting a nucleotide sequence of interest. A skilled artisan is aware which restriction enzyme sites would be useful for such a purpose. One skilled in the art is aware that the restriction sites themselves can be of any size or form, including a methylated form. Said restriction enzyme site can include any DNA sequence which is recognized by a specific restriction enzyme and could be a blunt-cutter restriction enzyme site or a non blunt-cutter restriction enzyme site.

The term "primary cell" as used herein is defined as a cell which can not be multiplied using endogenous machinery and gene products.

The term "promoter" as used herein is defined as the region of nucleotide sequence which regulates transcription of a specific nucleotide sequence, including enhancers, silencers and other cis-acting elements.

The term "reporter sequence" as used herein is defined as a nucleotide sequence which when expressed can be detected. The expressed product itself can be detected or a metabolite or other characteristic secondarily affected by the reporter product can be detected. The skilled artisan recognizes that any reporter sequence that could be detected by transcutaneous monitoring, by visualization with UV light, by visualization with infrared light, or by visualization with other imaging techniques, such as X-ray or MRI, would be of obvious value. Any tissue or body fluid or cell culture or cell free extract can be sampled depending on the reporter used. For example, secreted proteins, histological reporter and other reporter used by those skilled in the art may be utilized.

The term "RNA" as used herein is defined as ribonucleic acid.

The term "suicide nucleic acid sequence" as used herein is defined as a sequence in which the encoded gene product, upon exposure to a prodrug, facilitates death to a cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The term "T-antigen" as used herein is defined as a virally derived tumor-inducing agent or immortalization agent. Multiple examples exist in the art, including Simian Virus 40 T-antigen (SV-40 T-antigen).

The term "telomerase catalytic protein subunit" as used herein is defined as the amino acid sequence subunit of telomerase, which is a ribonucleoprotein.

The term "transcription" as used herein is defined as synthesis of an RNA from a DNA template.

The term "translation" as used herein is defined as synthesis of a protein from an RNA.

One specific embodiment of the present invention is a DNA sequence and fragments and derivatives thereof which functions as a bidirectional promoter. An additional embodiment is said DNA sequence selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31. In a specific embodiment said promoter promotes transcription of two separate nucleotide sequences wherein one of such nucleotide sequences is operatively linked to the 5' end of said promoter sequence and is transcribed 5' to 3' in the direction opposite from the 5' to 3' direction of said promoter sequence and the other of such nucleotide sequences is operatively linked to the 3' end of said promoter sequence and is transcribed 5' to 3' in the same direction as the 5' to 3' direction of said promoter sequence. In a specific embodiment said promoter promotes transcription of the said two nucleotide sequences in approximately equimolar amounts. In a specific embodiment said promoter is the aldehyde reductase promoter.

A further embodiment of the present invention is a recombinant DNA vector comprising said promoter or fragments and derivatives thereof when said promoter and fragments and derivatives thereof function as a bidirectional promoter; a first DNA sequence encoding a gene operatively linked to the 5' end of the promoter sequence wherein when said first DNA sequence is transcribed it is transcribed 5' to 3' in the direction opposite from the 5' to 3' direction of the promoter sequence; and a second DNA sequence encoding a gene operatively linked to the 3' end of the promoter sequence wherein when said second DNA sequence is transcribed it is transcribed 5' to 3' in the same direction as the 5' to 3' direction of the promoter sequence. In a specific embodiment, said vector also contains a poly A+ polyadenylation sequence operatively linked to the 3' end of at least one of said first or second nucleotide sequences. In an additional specific embodiment, said sequences are nonidentical.

In another embodiment at least one of said DNA sequences encodes a reporter sequence. In a specific embodiment said reporter sequence is selected from the group consisting of ampicillin, neomycin, kanamycin, luciferase, β-galactosidase, β-glucuronidase, chlorampenicol acetyl-transferase (CAT), blue fluorescent protein (BFP), green fluorescent protein (GFP), or placental alkaline phosphatase. In specific embodiments said nucleotide sequences encode heavy and light chains of an antibody, subunits of an interleukin, subunits of growth hormone receptor, the subunit of a homodimer, or subunits of a heterodimer. In an additional embodiment we claim the method of preparing said antibody, interleukin, growth hormone receptor, homodimer, and heterodimer comprising expression of said nucleotide sequences and the recovery of the formed protein. In a specific embodiment one nucleotide sequence encodes a therapeutic nucleotide sequence and the other nucleotide sequence encodes a suicide gene.

In another embodiment said recombinant DNA vector contains at least one nucleotide sequence which encodes a RNA; said RNA being the final product of said nucleotide sequence. In a further embodiment we claim the method of preparing a ribonucleoprotein containing an RNA and a protein encoded by said nucleotide sequences. In specific embodiments said RNA is the telomerase RNA, a snRNA, a snoRNA, a scRNA, an antisense RNA, or the XIST RNA.

An additional embodiment is the recombinant DNA vector comprising the promoter sequence selected from the group consisting of SEQ ID NO: 19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31 or fragments and derivatives thereof when said fragments and derivatives function as a bidirectional promoter; a first polylinker site into which a first DNA sequence is operatively linked to the 5' end of the promoter sequence wherein when said first DNA sequence is transcribed it is transcribed 5' to 3' in the direction opposite from the 5' to 3' direction of the promoter sequence; and a second polylinker site into which a second DNA sequence encoding a gene operatively linked to the 3' end of the promoter sequence wherein when said second DNA sequence is transcribed it is transcribed 5' to 3' in the same direction as the 5' to 3' direction of the promoter sequence.

An additional embodiment is said vector further comprising a poly A+ polyadenylation sequence operatively linked to the 3' end of at least one of said first or second nucleotide sequences.

One skilled in the art recognizes that there are a variety of reporter sequences which may be utilized. Reporter sequences can be selected from the group consisting of ampicillin, neomycin, kanamycin, luciferase, β-galactosidase, β-glucuronidase, chloramphenicol acetyltransferase (CAT), blue fluorescent protien, green fluorescent protein (GFP), or placental alkaline phosphatase. The reporter sequence does not have to be from the same organism as the non-reporter sequence but can be from a different organism. One strength of the invention is the use of reporter sequences that are easily detected or quantitated. Reporter genes that are useful particularly in mammals include secreted proteins, such as human growth hormone (HGH), human α-fetoprotein (hAFP), or mouse α-fetoprotein (mAFP), and in the mouse where sensitive assays can detect very low levels of compounds in biological fluids or tissues including the blood or urine that may have been secreted by a small number of cells in distant parts of the organism. In this case, the ease of detection does require sampling of biological fluids or tissues including blood or urine from each individual animal for quantitation of the reporter protein or a metabolite secondarily affected by the reporter protein. Other reporter proteins of interest would obviously include histological reporters such as chloramphenicol acetyltransferase (CAT), green fluorescent protein (GFP), β-galactosidase and β-glucuronidase. Luciferase is another widely utilized reporter gene. The reporter gene containing an epitope tag can also be monitored. In specific embodiments said reporter sequence is used for monitoring gene delivery of a sequence of interest or trafficking of a reporter gene product of interest.

In general, detection of the reporter means direct measurement or any other effect caused secondarily by the reporter, such as (1) change in the level of a metabolite in blood or urine, or (2) induction of drug resistance or sensitivity in whole animals or tissue culture cells.

In a specific embodiment, the sequences of the invention may be used for the expression of genes encoding proteins of interest in the pharmaceutical or foodstuffs sectors. By way of example, there may be mentioned enzymes (such as in particular superoxidedismutase, catalase, amylases, lipases, amidases, chymosin and the like), blood derivatives (such as serum albumin, alpha- or beta-globin, factor VIII, factor IX, von Willebrand factor, fibronectin, alpha-1-antitrypsin and the like), insulin and its variants, lymphokines (such as interleukins, interferons, colony stimulating factors (G-CSF, GM-CSF, M-CSF and the like), TNF, TRF and the like), growth factors (such as growth hormones, erythropoietin, FGF, EGF, PDGF, TGF and the like), apolipoproteins, antigenic polypeptides for the production of vaccines (hepatitis, cytomegalovirus, Epstein-Barr, herpes and the like) or alternatively polypeptide fusions such as in particular fusions comprising an active part fused with a stabilizing part (for example, fusions between albumin or fragments of albumin and the virus receptor or part of a virus receptor (such as CD4)).

In a specific embodiment, this system is particularly useful for expressing in the same host cell either a therapeutic gene and/or a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. This can be accomplished using the present invention by having one nucleotide sequence being the therapeutic gene linked to said promoter and having a second nucleotide sequence being the suicide gene also linked to said promoter. Thus, expression of the therapeutic gene in a host cell can be driven by said promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. Examples of therapeutic genes which may be used are genes whose products are related to cancer, heart disease, diabetes, cystic fibrosis, Alzheimer's disease, pulmonary disease, muscular dystrophy, or metabolic disorders.

In a preferred embodiment the present invention provides the application wherein two different components of a protein are generated and combine to get a full functional protein within the same cell.

An improvement over the related art is that one single promoter is utilized for production of two components in the same cell, and this promoter sequence contains no heterologous operator sequences or trans-acting factors produced from special cell lines. In contrast to the related art which assays a promoter linked to a reporter sequence in opposite orientations on separate constructs, the examples presented here demonstrate bidirectionality for a promoter in its native state by lying in a contiguous fashion with both genes, in opposite orientations, on the same molecule.

In related art, an IRES is used to produce two proteins within the same cell, which differs from the present invention. First, the means to generate two proteins using an IRES focuses on translation; that is, one bicistronic RNA is transcribed and two separate proteins are translated from a single transcript. In the present invention two separate transcripts are generated from a single promoter and are translated separately. Translation from an IRES in its native state is usually at reduced levels compared to the initial translation start site. This is in contrast to the strength of the present invention which can allow transcription of the two separate genes to approximately equimolar amounts.

Use of the Promoter of the Invention to Facilitate Cell Proliferation and Control In a specific embodiment the present invention comprises a recombinant DNA vector comprising a cassette, wherein said cassette comprises one DNA sequence which encodes a suicide nucleic acid sequence and the other DNA sequence which encodes an immortalization nucleic acid sequence, wherein the bidirectional promoter regulates transcription of the DNA sequences. In a specific embodiment the suicide nucleic acid sequence is thymidine kinase (TK). In another specific embodiment the immortalization nucleic acid sequence is selected from the group consisting of T-antigen, telomerase catalytic protein subunit and myc. A skilled artisan is aware how to obtain sequences of these examples by searching a sequence database, such as GenBank.

In another specific embodiment there is a method to initiate proliferation of a cell comprising the step of introducing the vector comprising a cassette, wherein said cassette comprises one DNA sequence which encodes a suicide nucleic acid sequence and the other DNA sequence which encodes an immortalization nucleic acid sequence, into said cell under conditions wherein activation of the bidirectional promoter to transcribe said immortalization nucleic acid sequence in said cell initiates proliferation of said cell. In another specific embodiment the vector further comprises excision sites flanking said cassette, wherein said excision sites are selected from the group consisting of lox, FLP recognition target sites, restriction endonuclease sites, and transposon sequences.

In an additional specific embodiment there is a method to initiate proliferation of a cell comprising the step of introducing a vector comprising a cassette, wherein said cassette comprises one DNA sequence which encodes a suicide nucleic acid sequence and the other DNA sequence which encodes an immortalization nucleic acid sequence, wherein the vector further comprises excision sites flanking said cassette, wherein said excision sites are selected from the group consisting of lox, FLP recognition target sites, restriction endonuclease sites, and transposon sequences, into said cell under conditions wherein activation of the bidirectional promoter to transcribe said immortalization nucleic acid sequence in said cell initiates proliferation of said cell. In a specific embodiment the introduction step further comprises integration of said excision sites and said cassette into a provirus of said cell. In an additional embodiment the method further comprises excising said immortalization nucleic acid sequence from said provirus through said excision sites. In a further specific embodiment the method further comprises destroying a cell which has failed to excise said immortalization nucleic acid sequence. In an additional specific embodiment the cell is a primary cell. In another specific embodiment the primary cell is selected from the group consisting of insulin-producing beta cell and liver cell. In another specific embodiment the primary cell is obtained from a patient, such as a primary insulin-producing beta cell from a diabetic patient.

The excision sites flanking either side of the cassette. In a specific embodiment the excision sites are selected from the group consisting of lox, FLP recognition target sites, restriction endonuclease sites, and transposon sequences. In a preferred embodiment the excision sites are recombination sites. In another preferred embodiment the excision sites are loxP sites. In the specific embodiment wherein the excision sites are restriction endonuclease sites, a skilled artisan is aware that these restriction endonuclease sites must not be present elsewhere in the DNA of the cell. A skilled artisan is also aware these sites may come from another organism, such as yeast. A skilled artisan is also aware how to deliver the restriction endonuclease to the cell, such as by adenoviral/retroviral mechanisms. In the specific embodiment wherein the excision sites are transposon sequences, a skilled artisan is aware the transposase must be provided for excision and means to do so.

Thus, a vector having a bidirectional promoter regulating transcription of an immortalization nucleic acid sequence, such as T-antigen, and a suicide nucleic acid sequence (or gene) is introduced to a primary cell which does not have the capability of proliferating to significant levels. Expression of the immortalization nucleic acid sequence, driven by the bidirectional promoter, facilitates proliferation of the cell. Once proliferation is no longer desired, excision of the cassette sequences, including the nucleotide sequences which encode the immortalization nucleic acid sequence and the suicide nucleic acid sequence, occurs through the excision sites. Subsequently, upon exposure of the cell to a prodrug (which, in conjunction with the product encoded by the suicide nucleic acid sequence, facilitates death), cells which have excised the immortalization nucleic acid sequence/suicide nucleic acid sequence are unaffected, whereas cells which have not excised the immortalization nucleic acid sequence/suicide nucleic acid sequence are killed.

Aldehyde Reductase Promoter Nucleic Acids and Uses Thereof

Certain aspects of the present invention concern at least one aldehyde reductase promoter nucleic acid. In certain aspects, the at least one aldehyde reductase promoter nucleic acid comprises a wild-type or mutant aldehyde reductase promoter nucleic acid. In certain aspects, the aldehyde reductase promoter nucleic acid comprises at least one nucleic acid segment of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; and SEQ ID NO:30, or at least one biologically functional equivalent thereof.

The present invention also concerns the isolation or creation of at least one recombinant construct or at least one recombinant host cell through the application of recombinant nucleic acid technology known to those of skill in the art or as described herein. The recombinant construct or host cell may comprise at least one aldehyde reductase promoter nucleic acid.

As used herein "wild-type" refers to the naturally occurring sequence of a nucleic acid at a genetic locus in the genome of an organism, and sequences transcribed or translated from such a nucleic acid. Thus, the term "wild-type" also may refer to the amino acid sequence encoded by the nucleic acid. As a genetic locus may have more than one sequence or alleles in a population of individuals, the term "wild-type" encompasses all such naturally occurring alleles. As used herein the term "polymorphic" means that variation exists (i.e. two or more alleles exist) at a genetic locus in the individuals of a population. As used herein "mutant" refers to a change in the sequence of a nucleic acid or its encoded protein, polypeptide or peptide that is the result of the hand of man.

A nucleic acid may be made by any technique known to one of ordinary skill in the art. Non-limiting examples of synthetic nucleic acid, particularly a synthetic oligonucleotide, include a nucleic acid made by in vitro chemically synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986, and U.S. Pat. Ser. No. 5,705,629, each incorporated herein by reference. A non-limiting example of enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of oligonucleotides described in U.S. Pat. No. 5,645,897, incorporated herein by reference. A non-limiting example of a biologically produced nucleic acid includes recombinant nucleic acid production in living cells, such as recombinant DNA vector production in bacteria (see for example, Sambrook et al. 1989, incorporated herein by reference).

A nucleic acid may be purified on polyacrylamide gels, cesium chloride centrifugation gradients, or by any other means known to one of ordinary skill in the art (see for example, Sambrook et al. 1989, incorporated herein by reference).

The term "nucleic acid" will generally refer to at least one molecule or strand of DNA, RNA or a derivative or mimic thereof, comprising at least one nucleobase, such as, for example, a naturally occurring purine or pyrimidine base found in DNA (e.g. adenine "A," guanine "G," thymine "T" and cytosine "C") or RNA (e.g. A, G, uracil "U" and C). The term "nucleic acid" encompass the terms "oligonucleotide" and "polynucleotide." The term "oligonucleotide" refers to at least one molecule of between about 3 and about 100 nucleobases in length. The term "polynucleotide" refers to at least one molecule of greater than about 100 nucleobases in length. These definitions generally refer to at least one single-stranded molecule, but in specific embodiments will also encompass at least one additional strand that is partially, substantially or fully complementary to the at least one single-stranded molecule. Thus, a nucleic acid may encompass at least one double-stranded molecule or at least one triple-stranded molecule that comprises one or more complementary strand(s) or "complement(s)" of a particular sequence comprising a strand of the molecule. As used herein, a single stranded nucleic acid may be denoted by the prefix "ss", a double stranded nucleic acid by the prefix "ds", and a triple stranded nucleic acid by the prefix "ts."

Thus, the present invention also encompasses at least one nucleic acid that is complementary to a SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 or SEQ ID NO:31 nucleic acid. In particular embodiments the invention encompasses at least one nucleic acid or nucleic acid segment complementary to the sequence set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. Nucleic acid(s) that are "complementary" or "complement(s)" are those that are capable of base-pairing according to the standard Watson-Crick, Hoogsteen or reverse Hoogsteen binding complementarity rules. As used herein, the term "complementary" or "complement(s)" also refers to nucleic acid(s) that are substantially complementary, as may be assessed by the same nucleotide comparison set forth above. The term "substantially complementary" refers to a nucleic acid comprising at least one sequence of consecutive nucleobases, or semiconsecutive nucleobases if one or more nucleobase moieties are not present in the molecule, are capable of hybridizing to at least one nucleic acid strand or duplex even if less than all nucleobases do not base pair with a counterpart nucleobase. In certain embodiments, a "substantially complementary" nucleic acid contains at least one sequence in which about 70%, about 75%, about 80%, about 85%, about 90%, about 95%, about 96%, about 97%, about 98%, about 99%, to about 100%, and any range therein, of the nucleobase sequence is capable of base-pairing with at least one single or double stranded nucleic acid molecule during hybridization. In certain embodiments, the term "substantially complementary" refers to at least one nucleic acid that may hybridize to at least one nucleic acid strand or duplex in stringent conditions. In certain embodiments, a "partly complementary" nucleic acid comprises at least one sequence that may hybridize in low stringency conditions to at least one single or double stranded nucleic acid, or contains at least one sequence in which less than about 70% of the nucleobase sequence is capable of base-pairing with at least one single or double stranded nucleic acid molecule during hybridization.

As used herein, "hybridization", "hybridizes" or "capable of hybridizing" is understood to mean the forming of a double or triple stranded molecule or a molecule with partial double or triple stranded nature. The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating at least one nucleic acid, such as a gene or nucleic acid segment thereof, or detecting at least one specific mRNA transcript or nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence of formamide, tetramethylammonium chloride or other solvent (s) in the hybridization mixture. It is generally appreciated that conditions may be rendered more stringent, such as, for example, the addition of increasing amounts of formamide.

It is also understood that these ranges, compositions and conditions for hybridization are mentioned by way of non-limiting example only, and that the desired stringency for a particular hybridization reaction is often determined empirically by comparison to one or more positive or negative controls. Depending on the application envisioned it is preferred to employ varying conditions of hybridization to achieve varying degrees of selectivity of the nucleic acid(s) towards target sequence(s). In a non-limiting example, identification or isolation of related target nucleic acid(s) that do not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

One or more nucleic acid(s) may comprise, or be composed entirely of, at least one derivative or mimic of at least one nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refers to a molecule that may or may not structurally resemble a naturally occurring molecule, but functions similarly to the naturally occurring molecule. As used herein, a "moiety" generally refers to a smaller chemical or molecular component of a larger chemical or molecular structure, and is encompassed by the term "molecule."

As used herein a "nucleobase" refers to a naturally occurring heterocyclic base, such as A, T, G, C or U ("naturally occurring nucleobase(s)"), found in at least one naturally occurring nucleic acid (i.e. DNA and RNA), and their naturally or non-naturally occurring derivatives and mimics. Non-limiting examples of nucleobases include purines and pyrimidines, as well as derivatives and mimics thereof, which generally can form one or more hydrogen bonds ("anneal" or "hybridize") with at least one naturally occurring nucleobase in manner that may substitute for naturally occurring nucleobase pairing (e.g. the hydrogen bonding between A and T, G and C, and A and U).

Nucleobase, nucleoside and nucleotide mimics or derivatives are well known in the art, and have been described in exemplary references such as, for example, Scheit, Nucleotide Analogs (John Wiley, New York, 1980), incorporated herein by reference. "Purine" and "pyrimidine" nucleobases encompass naturally occurring purine and pyrimidine nucleobases and also derivatives and mimics thereof, including but not limited to, those purines and pyrimidines substituted by one or more of alkyl, caboxyalkyl, amino, hydroxyl, halogen (i.e. fluoro, chloro, bromo, or iodo), thiol, or alkylthiol wherein the alkyl group comprises of from about 1, about 2, about 3, about 4, about 5, to about 6 arbon atoms. Non-limiting examples of purines and pyrimidines include deazapurines, 2,6-diaminopurine, 5-fluorouracil, xanthine, hypoxanthine, 8-bromoguanine, 8-chloroguanine, bromothymine, 8-aminoguanine, 8-hydroxyguanine, 8-methylguanine, 8-thioguanine, azaguanines, 2-aminopurine, 5-ethylcytosine, 5-methylcyosine, 5-bromouracil, 5-ethyluracil, 5-iodouracil, 5-chlorouracil, 5-propyluracil, thiouracil, 2-methyladenine, methylthioadenine, N,N-diemethyladenine, azaadenines, 8-bromoadenine, 8-hydroxyadenine, 6-hydroxyaminopurine, 6-thiopurine, 4-(6-aminohexyl/cytosine), and the like.

As used herein, "nucleoside" refers to an individual chemical unit comprising a nucleobase covalently attached to a nucleobase linker moiety. A non-limiting example of a "nucleobase linker moiety" is a sugar comprising 5-carbon atoms (a "5-carbon sugar"), including but not limited to deoxyribose, ribose or arabinose, and derivatives or mimics of 5-carbon sugars. Non-limiting examples of derivatives or mimics of 5-carbon sugars include 2'-fluoro-2'-deoxyribose or carbocyclic sugars where a carbon is substituted for the oxygen atom in the sugar ring. By way of non-limiting example, nucleosides comprising purine (i.e. A and G) or 7-deazapurine nucleobases typically covalently attach the 9 position of the purine or 7-deazapurine to the 1'-position of a 5-carbon sugar. In another non-limiting example, nucleosides comprising pyrimidine nucleobases (i.e. C, T or U) typically covalently attach the 1 position of the pyrimidine to 1'-position of a 5-carbon sugar(Komberg and Baker, DNA Replication, 2nd Ed. (Freeman, San Francisco, 1992). However, other types of covalent attachments of a nucleobase to a nucleobase linker moiety are known in the art, and non-limiting examples are described herein.

As used herein, a "nucleotide" refers to a nucleoside further comprising a "backbone moiety" generally used for the covalent attachment of one or more nucleotides to another molecule or to each other to form one or more nucleic acids. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when the nucleotide comprises derivatives or mimics of a naturally occurring 5-carbon sugar or phosphorus moiety, and non-limiting examples are described herein. The term nucleic acid sequence and nucleic acid may be used interchangeably herein.

A non-limiting example of a nucleic acid comprising such nucleoside or nucleotide derivatives and mimics is a "polyether nucleic acid", described in U.S. Pat. Ser. No. 5,908, 845, incorporated herein by reference, wherein one or more nucleobases are linked to chiral carbon atoms in a polyether backbone. Another example of a nucleic acid comprising nucleoside or nucleotide derivatives or mimics is a "peptide nucleic acid", also known as a "PNA", "peptide-based nucleic acid mimics" or "PENAMs", described in U.S. Pat. Ser. Nos. 5,786,461, 5891,625, 5,773,571, 5,766,855, 5,736,336, 5,719,262, 5,714,331, 5,539,082, and WO 92/20702, each of which is incorporated herein by reference. A peptide nucleic acid generally comprises at least one nucleobase and at least one nucleobase linker moiety that is either not a 5-carbon sugar and/or at least one backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

Peptide nucleic acids generally have enhanced sequence specificity, binding properties, and resistance to enzymatic degradation in comparison to molecules such as DNA and RNA (Egholm etal., Nature 1993,365,566; PCT/EP/01219). In addition, U.S. Pat. Nos. 5,766,855, 5,719,262, 5,714,331 and 5,736,336 describe PNAs comprising naturally and non-naturally occurring nucleobases and alkylamine side chains with further improvements in sequence specificity, solubility and binding affinity. These properties promote double or triple helix formation between a target nucleic acid and the PNA.

U.S. Pat. No. 5,641,625 describes that the binding of a PNA may to a target sequence has applications the creation of PNA probes to nucleotide sequences, modulating (i.e. enhancing or reducing) gene expression by binding of a PNA to an expressed nucleotide sequence, and cleavage of specific dsDNA molecules. In certain embodiments, nucleic acid analogues such as one or more peptide nucleic acids may be used to inhibit nucleic acid amplification, such as in PCR, to reduce false positives and discriminate between single base mutants, as described in U.S. Pat. Ser. No. 5891,625.

U.S. Pat. No. 5,786,461 describes PNAs with amino acid side chains attached to the PNA backbone to enhance solubility. The neutrality of the PNA backbone may contribute to the thermal stability of PNA/DNA and PNA/RNA duplexes by reducing charge repulsion. The melting temperature of PNA containing duplexes, or temperature at which the strands of the duplex release into single stranded molecules, has been described as less dependent upon salt concentration.

One method for increasing amount of cellular uptake property of PNAs is to attach a lipophilic group. U.S. application Ser. No. 1 17,363, filed Sep. 3, 1993, describes several alkylamino functionalities and their use in the attachment of such pendant groups to oligonucleosides.

In certain aspects, the present invention concerns at least one nucleic acid that is an isolated nucleic acid. As used herein, the term "isolated nucleic acid" refers to at least one nucleic acid molecule that has been isolated free of, or is otherwise free of, the bulk of the total genomic and transcribed nucleic acids of one or more cells, particularly mammalian cells, and more particularly human and mouse cells. In certain embodiments, "isolated nucleic acid" refers to a nucleic acid that has been isolated free of, or is otherwise free of, bulk of cellular components and macromolecules such as lipids, proteins, small biological molecules, and the like. As different species may have a RNA or a DNA containing genome, the term "isolated nucleic acid" encompasses both the terms "isolated DNA" and "isolated RNA". Thus, the isolated nucleic acid may comprise a RNA or DNA molecule isolated from, or otherwise free of, the bulk of total RNA, DNA or other nucleic acids of a particular species. As used herein, an isolated nucleic acid isolated from a particular species is referred to as a "species specific nucleic acid." When designating a nucleic acid isolated from a particular species, such as human, such a type of nucleic acid may be identified by the name of the species. For example, a nucleic acid isolated from one or more humans would be an "isolated human nucleic acid", a nucleic acid isolated from mouse would be an "isolated mouse nucleic acid", etc.

Of course, more than one copy of an isolated nucleic acid may be isolated from biological material, or produced in vitro, using standard techniques that are known to those of skill in the art. In particular embodiments, the isolated nucleic acid is capable of expressing a RNA, a protein, polypeptide or peptide. In other embodiments, the isolated nucleic acid comprises an isolated aldehyde reductase promoter.

Herein certain embodiments, a "gene" refers to a nucleic acid that is transcribed. As used herein, a "gene segment" is a nucleic acid segment of a gene. In certain aspects, the gene includes regulatory sequences involved in transcription, or message production or composition. In particular embodiments, the gene comprises transcribed sequences that encode for a protein, polypeptide or peptide. In keeping with the terminology described herein, an "isolated gene" may comprise transcribed nucleic acid(s), regulatory sequences, coding sequences, or the like, isolated substantially away from other such sequences, such as other naturally occurring genes, regulatory sequences, polypeptide or peptide encoding sequences, etc. In this respect, the term "gene" is used for simplicity to refer to a nucleic acid comprising a nucleotide sequence that is transcribed, and the complement thereof. In particular aspects, the transcribed nucleotide sequence comprises at least one functional protein, polypeptide and/or peptide encoding unit. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like. "Isolated substantially away from other coding sequences" means that the gene of interest, in this case the aldehyde reductase promoter, forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

In certain embodiments, the nucleic acid is a nucleic acid segment. As used herein, the term "nucleic acid segment" includes smaller fragments of a nucleic acid, such as for non-limiting example, those that are only part of the aldehyde reductase, of from about 2 nucleotides to the full length of the regulator region, or promoter region. In certain embodiments, the "nucleic acid segment" encompasses the full length aldehyde reductase promoter sequence. In preferred embodiments the nucleic acid segment and the smaller fragments or derivatives exhibit bidirectional promoter activity, and a skilled artisan has available herein methods regarding how to test these smaller fragments and various nucleic acid segments for bidirectional promoter function.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and/or so on. For a 15-mer, the nucleic acid segments correspond to bases 1 to 15, 2 to 16, 3 to 17 . . . and/or so on. For a 20-mer, the nucleic segments correspond to bases 1 to 20, 2 to 21, 3 to 22 . . . and/or so on. In certain embodiments, the nucleic acid segment may be a probe or primer. As used herein, a "probe" is defined as a nucleic acid which is used to identify a complementary nucleic acid. As used herein, a "primer" is defined as a relatively short nucleic acid which is used to initiate polymerization of a nucleic acid, and may be from about 8 nucleotides to about 30 nucleotides in length. A non-limiting example of this would be the creation of nucleic acid segments of various lengths and sequence composition for probes and primers based on the sequences disclosed in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31.

The nucleic acid(s) of the present invention, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is defined as a nucleic acid segment that contains multiple nucleic acid regions, including a nucleic acid sequence which is used to generate a gene product, such as an RNA or protein, a promoter, restriction sites, etc. The length overall length may vary considerably between nucleic acid constructs. Thus, a nucleic acid segment of almost any length may be employed, with the total length preferably being limited by the ease of preparation or use in the intended recombinant nucleic acid protocol.

In a non-limiting example, one or more nucleic acid constructs may be prepared that include a contiguous stretch of nucleotides identical to or complementary to SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. A nucleic acid construct may be about 5, about 10 to about 15, about 20, about 50, about 100, about 200, about 500, about 1,000, about 2,000, about 3,000, about 5,000, about 10,000, about 15,000, about 20,000, about 30,000, about 50,000, about 100,000, about 250,000, to about 500,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges", as used herein, means any length or range including or between the quoted values (i.e. all integers including and between such values). Non-limiting examples of intermediate lengths include about 11; about 21; about 51; about 101; about 151; about 1,001; about 50,001; about 750,001; about 1,000,001, etc. Non-limiting examples of intermediate ranges include about 3 to about 32, about 150 to about 500,001, about 3,032 to about 7,145, about 5,000 to about 15,000, about 20,007 to about 1,000,003, etc.

In certain embodiments, the nucleic acid construct is a recombinant vector. As used herein, a "recombinant vector" is a nucleic acid molecule which may contain multiple nucleic acid segments such as coding sequence, multiple cloning sites, an origin of replication, etc. In certain aspects, the recombinant vector is an expression cassette. As used herein, an expression cassette is a nucleic acid sequence which contains a nucleic acid to be expressed, such as for a RNA or a protein and the requisite sequences for its expression, such as a promoter.

In particular embodiments, the invention concerns one or more recombinant vector(s) comprising nucleic acid sequences that are a bidirectional promoter as essentially as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. In particular aspects, the recombinant vectors are DNA vectors.

The term "a sequence essentially as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 means that the sequence substantially corresponds to a portion of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. Thus, "a sequence essentially as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 encompasses nucleic acids, nucleic acid segments, and genes that comprise part or all of the nucleic acid sequences as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31.

In certain other embodiments, the invention concerns at least one recombinant vector that include within its sequence a nucleic acid sequence essentially as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. In particular embodiments, the recombinant vector comprises DNA sequences of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 that have bidirectional promoter activity.

It will also be understood that nucleic acid sequences may include additional residues, such as additional 5' or 3' sequences, or various combinations thereof, and yet still be essentially as set forth in one of the sequences disclosed herein, so long as the sequence meets the criteria set forth above, including the maintenance of biological activity where bidirectional expression of two gene products is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Nucleic acid sequences that have between about 70% and about 79%; or more preferably, between about 80% and about 89%; or even more particularly, between about 90% and about 99%; of nucleotides that are identical to the nucleotides of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 will be nucleic acid sequences that are "essentially as set forth in SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31".

It will also be understood that this invention is not limited to the particular nucleic acid or amino acid sequences of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. Recombinant vectors and isolated nucleic acid segments may therefore variously include these regulatory regions themselves.

As used herein an "organism" may be a prokaryote, eukaryote, virus and the like. As used herein the term "sequence" encompasses both the terms "nucleic acid" and "proteancecous" or "proteanaceous composition." As used herein, the term "proteinaceous composition" encompasses the terms "protein", "polypeptide" and "peptide." As used herein "artificial sequence" refers to a sequence of a nucleic acid not derived from sequence naturally occurring at a genetic locus, as well as the sequence of any proteins, polypeptides or peptides encoded by such a nucleic acid. A "synthetic sequence", refers to a nucleic acid or proteinaceous composition produced by chemical synthesis in vitro, rather than enzymatic production in vitro (i.e. an "enzymatically produced" sequence) or biological production in vivo (i.e. a "biologically produced" sequence).

NUCLEIC ACID-BASED EXPRESSION SYSTEMS

1. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

Naturally, it will be important to employ the promoter as it effectively directs the expression of the DNA segment in the cell type, organelle, and organism chosen for expression. The promoter may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

b. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

c. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

d. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

e. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

f. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, zeocin and histidinol are useful selectable markers. In addition to markers conferring a phenotype that allows for the discrimination of transformants based on the implementation of conditions, other types of markers including screenable markers such as GFP, whose basis is calorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

2. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE® Competent Cells and SOLOPACK™ Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. No. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an E. coli expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the Pichia methanolica Expression System, which is designed for high-level production of recombinant proteins in the methylotrophic yeast Pichia methanolica. One of skill in the art would know how to express a vector, such as an expression construct, to produce a nucleic acid sequence or its cognate polypeptide, protein, or peptide.

Derivatives of Aldehyde Reducatase Promoter Sequences

One aspect of the invention provides derivatives of specific promoters. One means for preparing derivatives of such promoters comprises introducing mutations into the promoter sequences. Such mutants may potentially have enhanced, reduced, or altered function relative to the native sequence or alternatively, may be silent with regard to function.

Mutagenesis may be carried out at random and the mutagenized sequences screened for function. Alternatively, particular sequences which provide the promoter region with desirable expression characteristics could be identified and these or similar sequences introduced into other related or non-related sequences via mutation. Similarly, non-essential elements may be deleted without significantly altering the function of the promoter. It is further contemplated that one could mutagenize these sequences in order to enhance their utility in expressing transgenes, especially in a gene therapy construct in humans.

The means for mutagenizing a DNA segment comprising a specific promoter sequence are well-known to those of skill in the art. Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, by introducing one or more nucleotide sequence changes into the DNA.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids also are routinely employed in site directed mutagenesis to eliminate the step of transferring the gene of interest from a plasmid to a phage.

Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols.

The preparation of sequence variants of the selected promoter or intron-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, incorporated herein by reference. A number of template dependent processes are available to amplify the target sequences of interest present in a sample, such methods being well known in the art and specifically disclosed herein.

One efficient, targeted means for preparing mutagenized promoters or enhancers relies upon the identification of putative regulatory elements within the target sequence. These can be identified, for example, by comparison with known promoter sequences. Sequences which are shared among genes with similar functions or expression patterns are likely candidates for the binding of transcription factors and are likely elements to confer tissue specific expression patterns.

One of skill in the art will recognize that regulatory elements may be included in regions of the gene other than the 5'-untranslated region, and comparison of coding and 3'-noncoding regions of genes may identify putative regulatory elements. Confirmation of putative regulatory elements can be achieved by deletion, duplication, or other alteration or mutation of each putative regulatory region followed by functional analysis of each construct by assay of a reporter gene which is functionally attached to each construct. As such, once a starting promoter sequence is provided, any of a number of different functional mutants of the starting sequence could be readily prepared using methods well known in the art (Zhang et al, 1997).

Mutation, alteration, duplication, or truncation mutants the promoter region of the invention could be randomly prepared or prepared by selection of regions identified as containing putative regulatory elements, and then assayed. With this strategy, a series of constructs are prepared, each containing a different portion of the clone (a subclone), either mutated or altered or containing wild-type sequence, and these constructs are then screened for activity. A suitable means for screening for activity is to attach such a promoter construct to a selectable or screenable marker gene and to assay for gene expression.

Other assays may be used to identify responsive elements in a promoter region or gene. Such assays will be known to those of skill in the art (see for example, Sambrook et al., 1989; Zhang et al, 1997; Shan et al., 1997; Dai and Burnstein, 1996; Cleutjens et al., 1997; Ng et al., 1994; Shida et al., 1993), and include DNase I footprinting studies, Elecromobility Shift Assay patterns (EMSA), the binding pattern of purified transcription factors, effects of specific transcription factor antibodies in inhibiting the binding of a transcription factor to a putative responsive element, Western analysis, nuclear run-on assays, and DNA methylation interference analyisis.

Preferred promoter constructs may be identified that retain the desired, or even enhanced, activity (e.g., bidirectional activity). The smallest segment required for activity may be identified through comparison of the selected deletion or mutation constructs. Once identified, such segments may be duplicated, mutated, or combined with other known or regulatory elements and assayed for activity or regulatory properties. Promoter region sequences used to identify regulatory elements can also be used to identify and isolate transcription factors that bind a putative regulatory sequence or element, according to standard methods of protein purification, such as affinity chromatography, as discussed above.

Potentially, identified promoter region sequences, whether used alone or combined with additional promoters, enhancers, or regulatory elements, will be induced and/or regulated by an external agent, such as a hormone, transcription factor, enzyme, or pharmaceutical agent, to express operatively linked genes or sequences (Zhang et al., 1997; Shan et al., 1997). Alternatively, such a construct may be designed to cease expression upon exposure to an external agent.

Additionally, deletion mutants may be produced and assayed essentially according to Matusik (U.S. Pat. No. 5,783,681, Jul. 21, 1998). Plasmids may be constructed containing the promoter adjacent to a reporter gene, for example CAT. The construct may be designed to contain additional regulatory sequences, such as polyadenylation, termination and cleavage signals. Deletion mutants may be prepared by a time course treatment of the isolated prostate specific transglutaminase promoter with Bal 31 exonuclease (for 15, 30, 45, 60 and 75 seconds, for example). Following limited digestion, the promoter sequence may be ligated to appropriate linker sequences and reinserted into the CAT expression vector. After transformation into an appropriate host DNAs digested with restriction enzymes that cut at sites flanking the promoter sequence. Promoter size may be determined by agarose gel electrophoresis according to standard techniques.

Following selection of a range of deletion mutants of varying size, the activities of the deleted promoters for expression of the linked CAT gene may be determined according to standard protocols.

The precise nature of the deleted portion of the promoter may be determined using standard DNA sequencing, such as Sanger dideoxy termination sequencing, to identify which promoter sequences have been removed in each of the assayed deletion mutants. Thus, a correlation may be obtained between the presence or absence of specific elements within the promoter sequence and changes in activity of the linked reporter gene.

Assays of Gene Expression

Assays may be employed within the scope of the instant invention for determination of the relative efficiency of gene expression. For example, assays may be used to determine the efficacy of deletion mutants of specific promoter regions in directing expression of operably linked genes. Similarly, one could produce random or site-specific mutants of promoter regions and assay the efficacy of the mutants in the expression of an operably linked gene. Alternatively, assays could be used to determine the function of a promoter region in enhancing gene expression when used in conjunction with various different regulatory elements, enhancers, and exogenous genes.

Gene expression may be determined by measuring the production of RNA, protein or both. The gene product (RNA or protein) may be isolated and/or detected by methods well known in the art. Following detection, one may compare the results seen in a given cell line or individual with a statistically significant reference group of non-transformed control cells. Alternatively, one may compare production of RNA or protein products in cell lines transformed with the same gene operably linked to various mutants of a promoter sequence. In this way, it is possible to identify regulatory regions within a novel promoter sequence by their effect on the expression of an operably linked gene.

Screenable markers constitute another efficient means for quantifying the expression of a given gene. Potentially any screenable marker could be expressed and the marker gene product quantified, thereby providing an estimate of the efficiency with which the promoter directs expression of the gene. Quantification can readily be carried out using either visual means, or, for example, a photon counting device.

Nucleic Acid Detection

In addition to their use to direct expression of a specific nucleic acid, the nucleic acid sequences such as SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; and SEQ ID NO:30 disclosed herein have a variety of other uses. For example, they have utility as probes or primers for embodiments involving nucleic acid hybridization.

1. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM MgCl2, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl2, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

2. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from eight to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assy (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989).

3. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

4. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substititution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

5. Kits

All the essential materials and/or reagents required for detecting SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31 in a sample may be assembled together in a kit. This generally will comprise a probe or primers designed to hybridize specifically to individual nucleic acids of interest in the practice of the present invention, including SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and/or SEQ ID NO:31. Also included may be enzymes suitable for amplifying nucleic acids, including various polymerases (reverse transcriptase, Taq, etc.), deoxynucleotides and buffers to provide the necessary reaction mixture for amplification. Such kits may also include enzymes and other reagents suitable for detection of specific nucleic acids or amplification products. Such kits generally will comprise, in suitable means, distinct containers for each individual reagent or enzyme as well as for each probe or primer pair.

Gene Therapy Administration

For gene therapy, a skilled artisan would be cognizant that the vector to be utilized must contain the gene of interest operatively linked to a promoter. For antisense gene therapy, the antisense sequence of the gene of interest would be operatively linked to a promoter. One skilled in the art recognizes that in certain instances other sequences such as a 3' UTR regulatory sequences are useful in expressing the gene of interest. Where appropriate, the gene therapy vectors can be formulated into preparations in solid, semisolid, liquid or gaseous forms in the ways known in the art for their respective route of administration. Means known in the art can be utilized to prevent release and absorption of the composition until it reaches the target organ or to ensure timed-release of the composition. A pharmaceutically acceptable form should be employed which does not ineffectuate the compositions of the present invention. In pharmaceutical dosage forms, the compositions can be used alone or in appropriate association, as well as in combination, with other pharmaceutically active compounds. A sufficient amount of vector containing the therapeutic nucleic acid sequence must be administered to provide a pharmacologically effective dose of the gene product.

One skilled in the art recognizes that different methods of delivery may be utilized to administer a vector into a cell. Examples include: (1) methods utilizing physical means, such as electroporation (electricity), a gene gun (physical force) or applying large volumes of a liquid (pressure); and (2) methods wherein said vector is complexed to another entity, such as a liposome or transporter molecule.

Accordingly, the present invention provides a method of transferring a therapeutic gene to a host, which comprises administering the vector of the present invention, preferably as part of a composition, using any of the aforementioned routes of administration or alternative routes known to those skilled in the art and appropriate for a particular application. Effective gene transfer of a vector to a host cell in accordance with the present invention to a host cell can be monitored in terms of a therapeutic effect (e.g. alleviation of some symptom associated with the particular disease being treated) or, further, by evidence of the transferred gene or expression of the gene within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer).

These methods described herein are by no means all-inclusive, and further methods to suit the specific application will be apparent to the ordinary skilled artisan. Moreover, the effective amount of the compositions can be further approximated through analogy to compounds known to exert the desired effect.

Furthermore, the actual dose and schedule can vary depending on whether the compositions are administered in combination with other pharmaceutical compositions, or depending on interindividual differences in pharmacokinetics, drug disposition, and metabolism. Similarly, amounts can vary in in vitro applications depending on the particular cell line utilized (e.g., based on the number of vector receptors present on the cell surface, or the ability of the particular vector employed for gene transfer to replicate in that cell line). Furthermore, the amount of vector to be added per cell will likely vary with the length and stability of the therapeutic gene inserted in the vector, as well as also the nature of the sequence, and is particularly a parameter which needs to be determined empirically, and can be altered due to factors not inherent to the methods of the present invention (for instance, the cost associated with synthesis). One skilled in the art can easily make any necessary adjustments in accordance with the exigencies of the particular situation.

It is possible that cells containing the therapeutic gene may also contain a suicide gene (i.e., a gene which encodes a product that can be used to destroy the cell, such as herpes simplex virus thymidine kinase). In many gene therapy situations, it is desirable to be able to express a gene for therapeutic purposes in a host cell but also to have the capacity to destroy the host cell once the therapy is completed, becomes uncontrollable, or does not lead to a predictable or desirable result. Thus, expression of the therapeutic gene in a host cell can be driven by a promoter although the product of said suicide gene remains harmless in the absence of a prodrug. Once the therapy is complete or no longer desired or needed, administration of a prodrug causes the suicide gene product to become lethal to the cell. Examples of suicide gene/prodrug combinations which may be used are Herpes Simplex Virus-thymidine kinase (HSV-tk) and ganciclovir, acyclovir or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside.

The method of cell therapy may be employed by methods known in the art wherein a cultured cell containing a copy of a nucleic acid sequence or amino acid sequence of a sequence of interest is introduced.

These methods described herein are by no means all-inclusive, and further methods to suit the specific application will be apparent to the ordinary skilled artisan. Moreover, the effective amount of the compositions can be further approximated through analogy to compounds known to exert the desired effect.

The following examples are offered by way of example and are not intended to limit the scope of the invention in any manner.

EXAMPLE 1

Isolation of Aldehyde Reductase cDNA From Adrenal Library

In the course of screening a human adrenal cDNA library for aldo-keto reductases, a cDNA clone coding for aldehyde reductase was isolated (SEQ ID NO:17). This clone was identical in its coding and 3' untranslated regions to the previously reported liver and placental aldehyde reductase cDNAs (Bohren et al., 1989). However, as shown in FIG. 2, the two sets of clones were totally different in their 5' untranslated regions. The basis for this discrepancy became clear upon cloning of the human aldehyde reductase gene.

EXAMPLE 2

Cloning of the Aldehyde Reductase Gene

Screening of the human genomic phage library with human liver aldehyde reductase cDNA gave several positive clones. A human genomic library in EMBL-3 (Clontech) was screened at high stringency (65° C. and 1×SSC) with a full-length human liver aldehyde reductase cDNA probe (Bohren et al., 1989) (SEQ ID NO:18) that was randomly primed using $^{32}$P labeled dCTP. Positive clones were isolated, cut into smaller fragments with various restriction enzymes, and subcloned into pGem3 vector (Promega) for restriction mapping and sequencing. Sequencing was performed by the Sanger method (USB sequencing kit). The whole coding region, but not the 5' untranslated region, was found on these clones. Exons 3 through 8 were found and completely sequenced on a single 4.2 kb PstI-BamHI DNA fragment isolated from the largest phage clone identified and subcloned into pGEM-3. Exon 2 was identified on a separate subcloned fragment that overlapped with the 4.2 kb PstI-BamHI DNA fragment on one end, and a BamHI fragment containing exon 9 was directly adjacent to the 3' end of the 4.2 kb PstI-BamHI DNA. However, the 5' untranslated region of the cDNA could not be found on the genomic clones despite numerous screenings of the phage library and examination of several phage clones. The failure to find the 5' untranslated regions warranted a screen for a human BAC library by PCR using intron primers flanking exon 4.

EXAMPLE 3

Isolation of Full Length Aldehyde Reductase Gene From a BAC Library

A human bacterial artificial chromosome (BAC) library was screened by PCR in two steps as recommended by the manufacturer (Research Genetics; Huntsville, Ala.). Two primers 5'-GGTGAGACCACGTGCTCATGGCT-3' (SEQ ID NO:6), and 5'-GCATGCCAAGCTGAGGAGCTTGAC-3' (SEQ ID NO:7), located in the intron areas upstream and downstream of exon 4, generated a 334 bp amplimer which was used to screen for the positive clone (clone 112J8). DNA from this clone was purified using a plasmid purification kit (Qiagen; Valencia, Calif.), digested with several restriction enzymes, and tested for the presence of the missing 5' exons by Southern blot analysis. Primers 5'-TATTCACGCTCTGTGCTTGTGCCAAG-3' (SEQ ID NO:8) and 5'-AGCAGCAGCTAGCCAGGCAAAG-3' (SEQ ID NO:9), derived from the 5' untranslated region of adrenal and liver cDNA isoforms, respectively, were end-labeled with $^{32}$P-γATP and used as probes. Both primers hybridized to a 4.2 kb BamHI fragment of the BAC indicating that the corresponding sequences are present on the genomic DNA. This fragment was subcloned into pSP73 vector (Promega) and sequenced by automated sequencing (Applied Biosystems), and on occasion confirmed by manual sequencing. Both untranslated regions were found on this fragment, each coded by a separate exon (exons 1a and 1b), with a 1.3 kb intron between them. An 8.2 kb XbaI fragment overlapping with the 4.2 kb BamHI piece, but stretching 5 kb farther upstream, was also subcloned and its partial sequence containing the 5'-end of the gene and the putative promoter was obtained. To determine the distance between the newly found 5' exons and the first coding exon (exon 2), BAC DNA was digested with several rare cutting enzymes and probed with exon 1a and exon 2 probes, (5'-TATTCACGCTCTGTGCTTGTGCCAAG-3') (SEQ ID NO:10), and (5'-AGTAGAACACAGGAAGCCGCCAT-3') (SEQ ID NO:11), respectively. The patterns obtained with the two probes were compared with each other and a restriction map of the intron 1 area was composed. A 7.8 kb XbaI-NcoI fragment, encompassing most of intron 1 was also subcloned, subjected to restriction mapping, and its ends sequenced. This fragment overlaps with the BamHI fragment of the BAC at its upstream side and with the fragment isolated from the phage library on its downstream side, completing a contiguous sequence of the aldehyde reductase gene.

Figure 3:
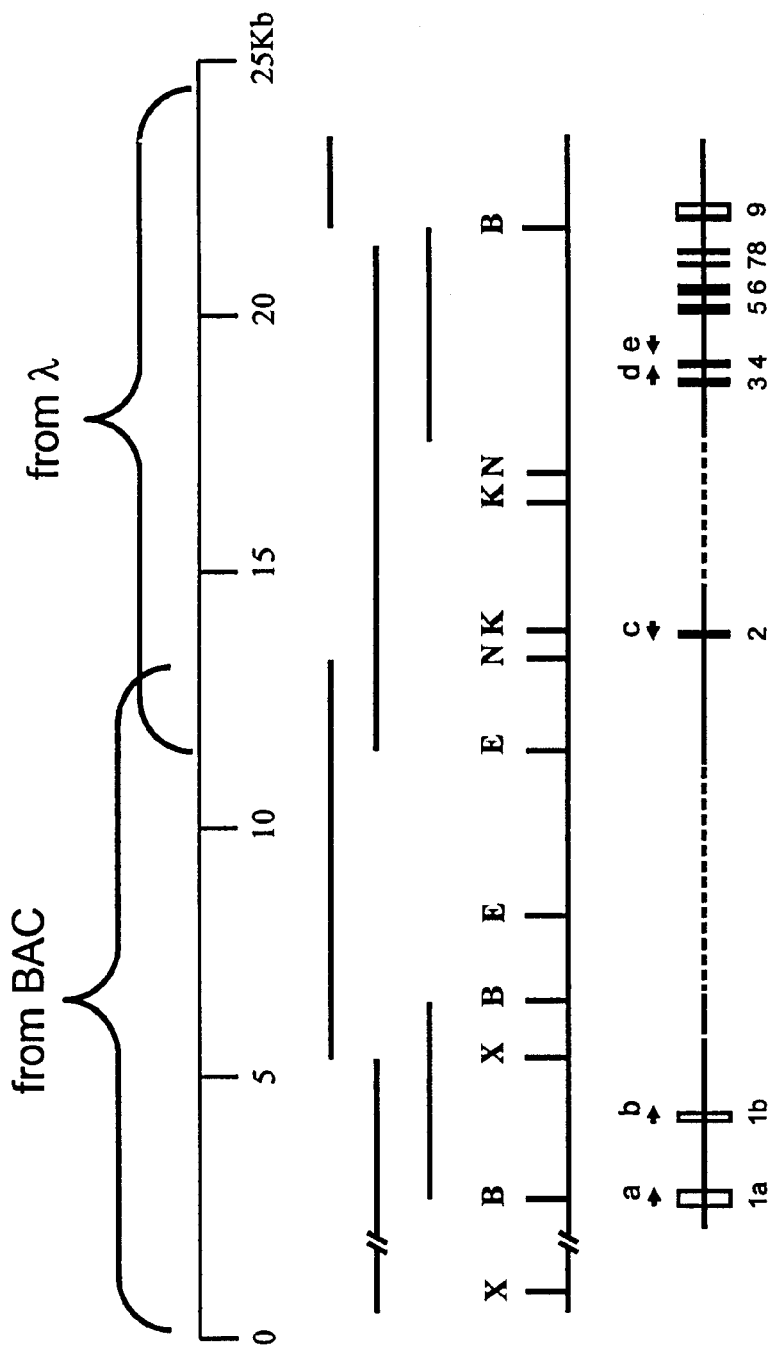
FIG. 3 illustrates a map of the aldehyde reductase gene. Overlapping fragments subcloned into general cloning vectors from λ and BAC clones are on top. A restriction map obtained with 5 enzymes (XbaI, BamHI, EcoRI, NcoI, and KpnI) is in the middle, and the location of introns and exons are on the bottom. Coding exons are shown as filled boxes, and non-coding. exons are shown as open boxes. Dashed lines represent unsequenced gaps.

The resulting clone (112J8) containing the full-length aldehyde reductase gene was analyzed by restriction mapping and sequencing using primers derived from the cDNA. The BAC clone contained the 5' untranslated sequences from both adrenal and liver aldehyde reductase cDNAs as was initially determined by Southern blotting and further confirmed by sequencing of the subcloned fragments. FIG. 3 shows a detailed map of the aldehyde reductase gene, which consists of 10 exons and spans approximately 20 kb of genomic DNA. Four contiguous parts of sequence were obtained (3861 bp, 649 bp, 3610 bp, and 4713 bp). Two intervening stretches of DNA (approximately 4.5 kb between exon 1b and exon 2, and approximately 3.0 kb between exons 2 and 3) were not sequenced. The furthest upstream segment contains exon 1a which has the 5'-untranslated sequence found in the adrenal cDNA, and is followed by exon 1b which codes for the corresponding sequence from the liver cDNA clone. These two exons are separated from each other by a 1.3 kb intron, and by a large intron of 9.4 kb from exon 2, where the initiation ATG codon is located. The last exon (exon 9) contains the stop codon as well as the full 3'-untranslated sequence including a polyadenylation signal.

Exons range in size from 73 to 328 bp, while introns range from 180 bp to 9.4 kb. A total of 24 repeats of the SINE (short interspersed DNA repetitive elements) and LINE (long Linterspersed DNA repetitive elements) families were found (Smit, 1998) in the sequenced part of the aldehyde reductase gene. These repeats compose 41% of the sequenced bases and almost all of them are located in the 5' part of the gene with only 2 alu repeats found between exons 3 and 9. A 77 bp simple repeat $(CATA)_n$ (SEQ ID NO:4) is found between exons 1a and 1b.

EXAMPLE 4

Alternative Splicing of the Aldehyde Reductase Gene

Figure 4:
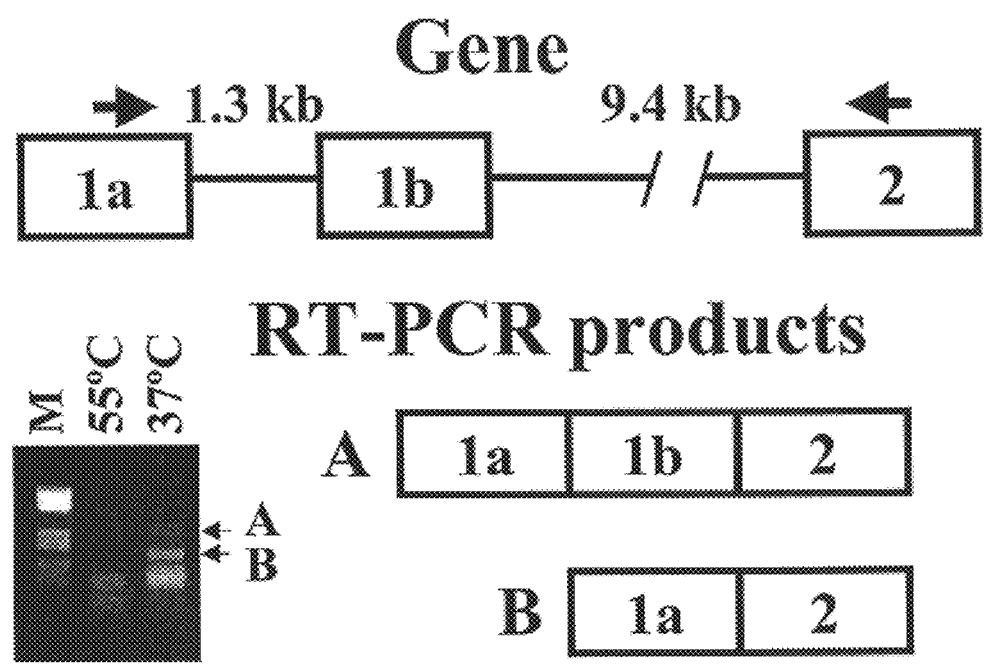
FIG. 4 demonstrates alternative splicing of the aldehyde reductase gene. The structure of the 5' part of the gene is shown on top with the location of PCR primers shown as arrows. Reaction products were sequenced completely, and their structure is shown with the drawing on the right. Boxes represent exons.

To explore the possibility of alternative splicing, the aldehyde reductase mRNA was examined by reverse transcription/PCR (RT-PCR). Hep G2 poly-A RNA (3 μg) was annealed to 25 ng of an antisense primer (5'-TGACCAGGCTCACTCTTCCAGGTACCCAGAC-3') (SEQ ID NO:12) derived from the exon 2 coding region for 15 min at 65° C. and chilled on ice. The full reaction mix for the reverse transcription reaction with avian myeloblastosis virus reverse transcriptase (Boehringer) was added, and the reaction performed at 55° C. or 37° C. for 1.5 hrs. The reaction mixture was diluted 10-fold with 10 mM Tris/10 mM EDTA, pH 7.5 buffer, and a 2.5 μl aliquot of this dilution was used as a template in a 50 μl PCR reaction with the primers 5'-CTCACCGCTAGACTTAAGCTGA-GGATCG-3' (SEQ ID NO:13) and 5'-AATCAGAGGCATCTTCTGCCCAGT-3' (SEQ ID NO:14) with the following cycling parameters: 94° C. for 1 min followed by 40 cycles of 94° C. for 1 min, 55° C. for 2 min, and 72° C. for 2 min. The reaction was resolved by electrophoresis on a 2% agarose gel. The PCR reaction gave two products that appeared to correspond to two splice variants as shown in FIG. 4. In fact, several PCR reactions performed with different primer pairs, one in exon 1a and the other in exon 2, always produced two products (as in FIG. 4) whereas a primer pair in exon 1b and exon 2 gave only one product. The bands corresponding to the reaction products were excised, cloned into PCR vector (Invitrogen), and sequenced. The shorter product (variant B) has exon 1a attached directly to exon 2, giving a sequence identical to the sequence of the adrenal cDNA. The larger product additionally contains exon 1b. Exon 1b is 128 bp long and contains 54 bp of the liver cDNA sequence plus an additional 5' fragment of 74 bp. This exon obeys classical AG-GT splicing rules on both sides, and comparison of the splice sites beyond the AG-GT border of exon 1b with other exons of the aldehyde reductase gene did not reveal any significant differences that might suggest a basis for alternative splicing of this exon. The cDNA cloned from the adrenal cDNA library corresponds to the shorter mRNA isoform, not containing exon 1b, and the cDNA from the liver library is a longer isoform with an incomplete 5' end. Therefore, both mRNA isoforms originate from alternative splicing of a single primary transcript that starts from exon 1a.

EXAMPLE 5

Primer Extension

Figure 5:
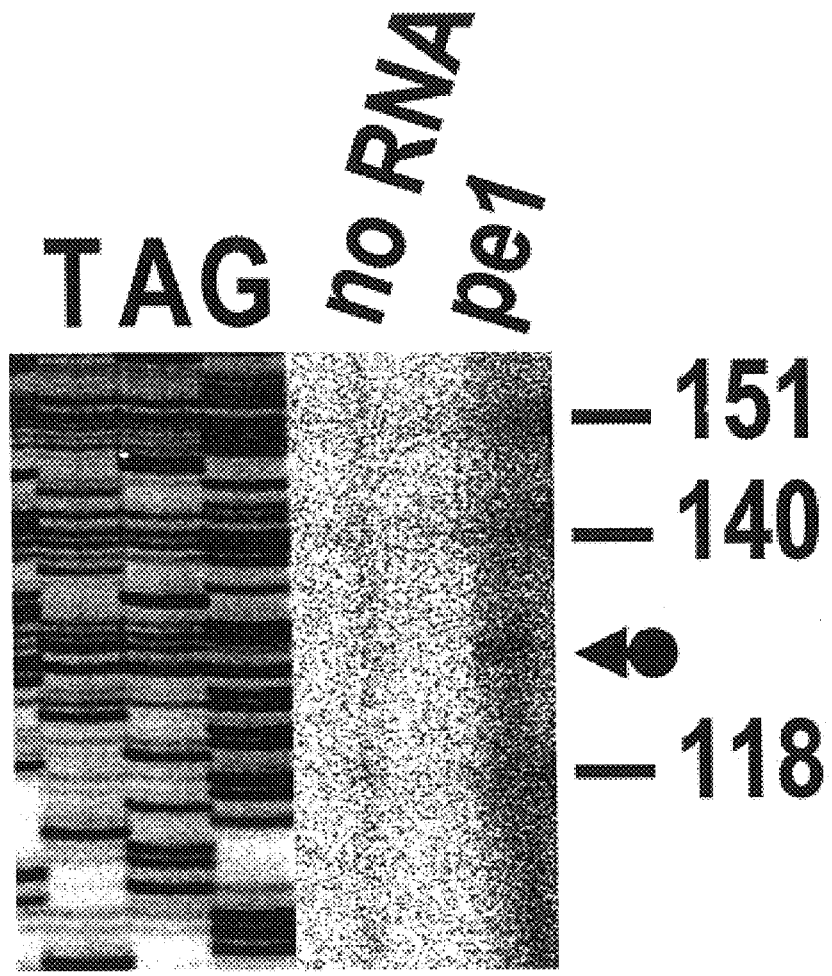
FIG. 5 shows determination of the transcription start site by primer extension. Primer pel (SEQ ID NO:5) was end-labeled, annealed to RNA isolated from HepG2 cells, and the products of the extension reaction were separated on a polyacrylamide gel. The location of molecular size markers is shown to the right of the gel. The left part represents a sequencing ladder generated with the same primer using cloned genomic DNA, and run on the same gel as the extension reaction. The right hand panel was enhanced using imaging software (Adobe Photoshop 3.0)

The transcription start site was determined by primer extension on poly-A RNA from HepG2 cells as follows. Poly-A RNA from Hep G2 cells was purified using a mRNA purification kit from Ambion, Inc., and checked for integrity by northern blot with a liver aldehyde reductase cDNA probe. A 25-mer antisense oligonucleotide (5'-GATGGAAAACAG-AGCTGGGAGGTAG-3') (SEQ ID NO:5) was gel-purified and end-labeled using $^{32}$P-γATP and T4 polynucleotide kinase (USB). Poly-A RNA (3.4 µg) was annealed with the primer for 3 min at 65° C., then slowly cooled to room temperature for 10 min. The extension reaction was carried out using the Promega primer extension kit at 40° C. or 50° C. for 40 min. The reaction was stopped by addition of loading buffer and denatured for 10 min at 100° C., prior to loading on a denaturing polyacrylamide gel next to a sequencing ladder obtained with the same primer, as well as molecular weight standards. FIG. 5 shows that the reaction product is a single band indicating a single major transcription start site. The start site is located 329 bp upstream from the 3' end of exon 1a.

EXAMPLE 6

Tissue Distribution of the Two mRNA Isoforms

Figure 6:
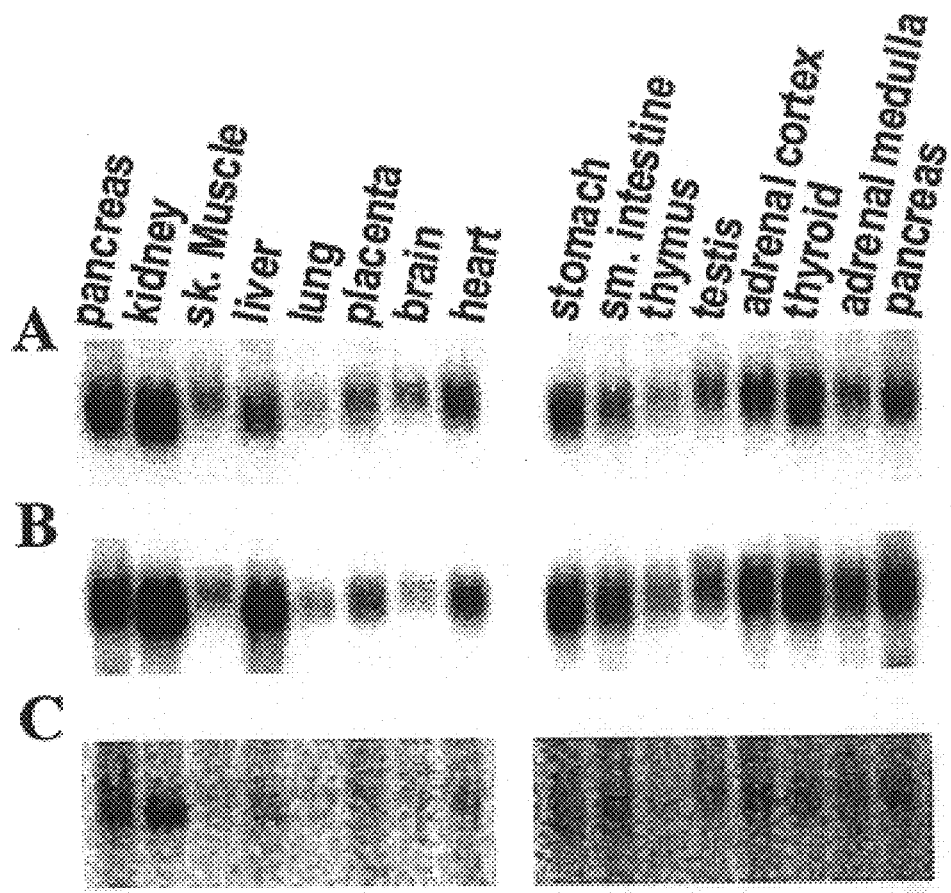
FIG. 6 shows northern blots of multiple human tissues. The probes used are: whole aldehyde reductase cDNA (short isoform) for A; exon 1a for B, and exon 1b for C.

Northern blots of several human tissues were hybridized with probes from exon 1a, 1b, and the entire cDNA to determine the tissue specificity of the two aldehyde reductase mRNA isoforms. Northern blots of various human tissues were purchased from Clontech. Each lane contained approximately 2 µg of poly-A RNA from each tissue immobilized on a charge-modified nylon membrane. Probes for alternative transcripts were generated by nick-translation. Membranes were hybridized following the recommended protocol (Clontech) and subjected to autoradiography or read on a phosphorimager (Molecular Dynamics). After each hybridization the probe was removed by a 20 min incubation in 0.5% SDS in water at 90–100° C. The completeness of probe removal was verified by an overnight (or longer, if longer exposure times were used) exposure to X-ray film. Exon 1a probe was used first, followed by several exon 1b probes, and finally the whole cDNA probe. The whole cDNA probe identified a band of approximately 1.5 kb present in every tissue (FIG. 6A). The highest levels were observed in kidney, followed by liver, thyroid, pancreas, stomach and adrenal cortex. The exon 1a probe (302 bp) contained part of exon 1a starting downstream from the BamHI site and 61 bp of the psp 73 vector. This probe demonstrated essentially the same pattern of tissue distribution as the entire cDNA probe (FIG. 6B). The result is consistent with our conclusion that exon 1a is present in both mRNA isoforms. Exon 1b contains 70 bp of repetitive alu sequence at the 5' end, and a high background was observed when the whole exon as a probe was used. Therefore, a probe was used that contained only 57 bp of the unique sequence of this exon and approximately 150 bp of the downstream intron. This probe gave a much weaker signal on a higher background as compared to the two other probes (FIG. 6C) indicating a low abundance of the splice variant containing exon 1b, although the tissue distribution demonstrated a similar pattern to that generated with the two other probes (FIGS. 5A and 5B). Thus, it appears that the two isoforms of the aldehyde reductase RNA are not differentially expressed in these tissues.

EXAMPLE 7

Functional Analysis of the Aldehyde Reductase Promoter

The region spanning approximately 600 bp upstream from the transcription start site was examined for the presence of typical promoter elements using the computer software, Matinspector (Quandt et al., 1995). The putative promoter does not contain a TATA box (FIG. 7), but a CAAT box was found at an atypical location 287 bp upstream from the transcription start site. A CAAT-like sequence, GCAAT, is found at position-58, which is a possible binding site for a member of C/EBP (CAAT enhancer binding protein) family of transcription factors, CHOP (C/EBP homology protein) (Ubeda et al., 1996a). The promoter region contains multiple GC-rich islands, and a SP-1 binding element located within 30 bp of the transcription start site which may play a role in determining transcription initiation. Several other potential transcription factor binding sites are noted in FIG. 7. The GenBank accession number is AF 112482.

A series of luciferase reporter constructs were generated by inserting various fragments of aldehyde reductase genomic DNA into a pGL3-basic vector upstream from the firefly luciferase reporter gene. DNA fragments for insertion into the reporter vector were generated by PCR on a template DNA from the promoter region (the XbaI 8.2 kb fragment) with primers containing specific restriction sites. Vent polymerase (New England Biolabs, Inc.) that has a proofreading activity was used to minimize errors. Amplified fragments were inserted into the vector pGL3-basic from Promega upstream of the firefly luciferase gene in forward or both orientations when necessary. Constructs were propagated in XL-1 blue strain of *E. coli* and the plasmid DNA was purified using Qiagen Maxi columns. All of the plasmid constructs were verified by DNA sequencing.

Promoter activities were assessed in transient transfections into HepG2 cells and subsequent measurements of luciferase activity by dual-luciferase assays. The HepG2 cell line (American Type Culture Collection; http://phage.atcc.org/searchengine/all.html) was maintained in a low glucose concentration (5.6 mM) Dulbecco's modified Eagle's medium supplemented with 10% fetal calf serum, 2 mM L-glutamine, 50 U/ml penicillin, and 50 µg/ml streptomycin. Transient transfections were performed using the calcium phosphate precipitation method as described earlier (Wang et al., 1993). Cells were divided into 24 well plates ($6\times10^5$ cells per well) and transfected one day later with 1 µg DNA of the construct to be tested. Transfection efficiency was determined by co-transfection with 0.2 µg of the vector pRL-TK, which expresses Renilla luciferase under control of the thymidine kinase promoter. Dual-luciferase assays were carried out 48 hrs after transfection using the dual-luciferase kit made by Promega. Briefly, cells were harvested using Passive Lysis Buffer, and 2 µl of cell extract was used to measure activity of the two luciferases in the same assay. After normalization by the Renilla luciferase control, the promoter activity was calculated as a percentage of the activity of the −416 to +86 construct, which was assayed in each experiment, assigned a 100% value and used to normalize the values.

Figure 8:
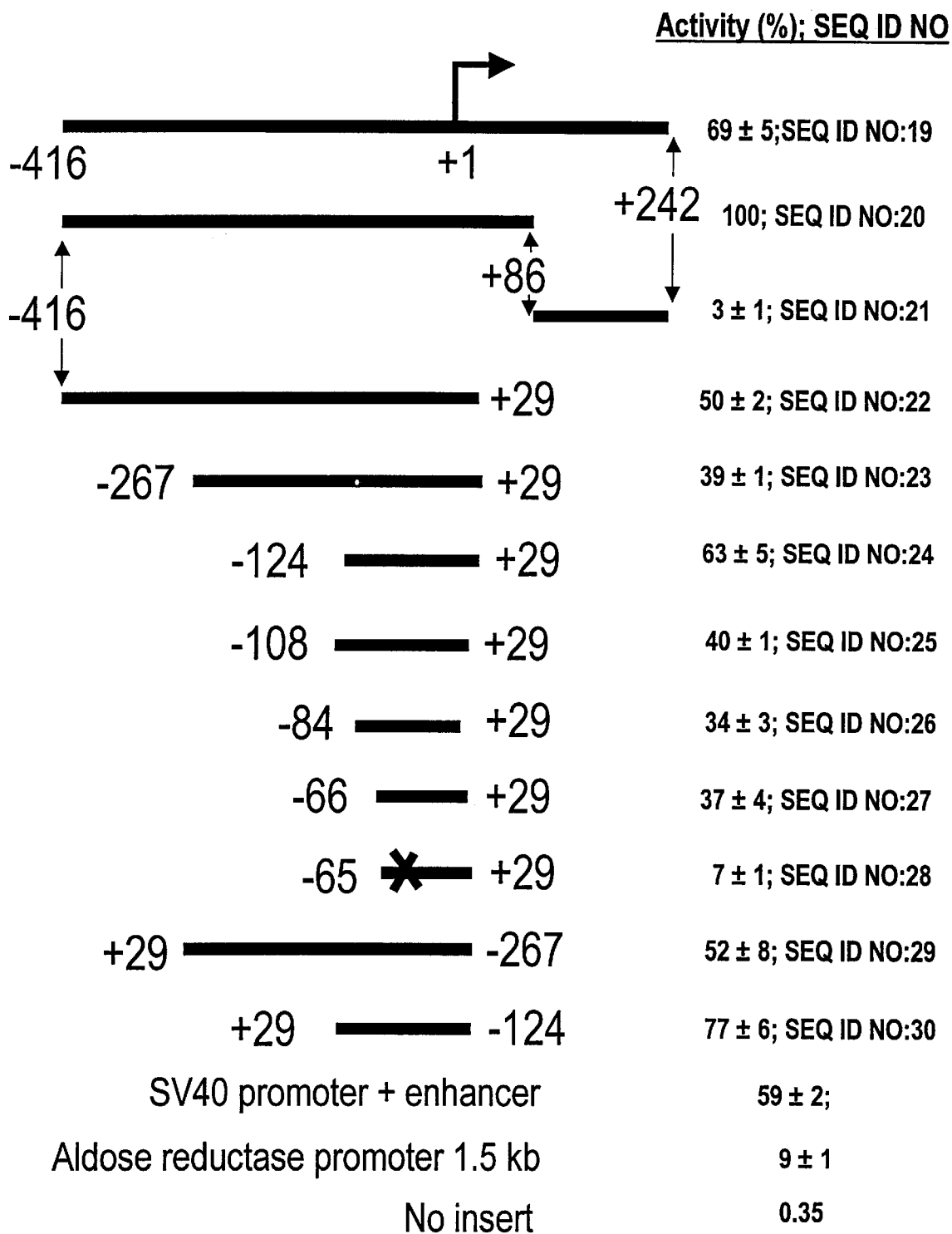
FIG. 8 illustrates deletion analysis of the promoter activity. The lines represent the size of various DNA fragments inserted into the pGL3 reporter vector. The arrow shows the location of the transcription start site, to which position number +1 is ascribed. Numbers on both sides of the lines show positions of the ends. A cross on the −65 to +29 construct represents two nucleotide mutations introduced into the putative CHOP binding site as described in Example 7.

FIG. 8 demonstrates several reporter constructs with varying regions of the aldehyde reductase promoter and their corresponding identifiers as SEQ ID NO:19 through SEQ ID NO:30. FIG. 8 shows that the region 5' to the transcription start site has strong promoter activity, comparable to that of the SV-40 promoter and enhancer. The highest activity was observed with an insert spanning −416 to +86 (SEQ ID NO:20), which had an average 290-fold (n=5) increase over the activity of the basic pGL3 vector without the insert. Both deletion and addition of sequence at the 3' end attenuated the activity to 50–60% of the −416 to +86 (SEQ ID NO:20) fragment, suggesting the presence of minor enhancers and silencers in this area (inserts −416 to +29 (SEQ ID NO:22), and −416 to +242 (SEQ ID NO:219)). Deletion of the upstream SPI and CAAT elements in construct −267 to +29 (SEQ ID NO:23) did not influence the promoter activity. Placement of fragments (−267 to +29 (SEQ ID NO:23)) and (−124 to +29 (SEQ ID NO:24)) in the reverse orientation in the construct gave nearly identical or even higher expression of the luciferase reporter gene than in the forward orientation. This finding suggests that the aldehyde reductase gene possesses a bidirectional promoter.

Additional 5' deletions to −66 also did not affect promoter activity indicating that the sequence between −416 and −66 does not have a major influence on promoter activity. Similarly, mutations of nucleotides within the possible binding sites of transcription factors elk1 and mzf1 (G-92→T, A-91→C) and (C-98→T, and C-97→T) also had no effect on reporter gene expression. However, mutation of two nucleotides in the putative CHOP binding site (G-58→A and A-56→C in the −65 to +29 construct) caused a substantial loss of luciferase reporter gene activity of more than 5-fold. It is thus likely that the CHOP binding element plays a major role in determining aldehyde reductase promoter activity.

A 1.5 kb fragment of aldose reductase promoter (Wang et al., 1993; Ko et al., 1997) inserted in the same luciferase reporter construct exhibits only 9% of the activity of the aldehyde reductase promoter in HepG2 cells, indicating that the aldehyde reductase promoter is much stronger at least in this cell type. The relative strength of the aldehyde reductase promoter may be a reflection of the fact that aldehyde reductase is expressed in higher quantities in the liver which is the source of the HepG2 cell line.

EXAMPLE 8

Characterization of the Promoter by Gel Mobility Shift Studies

Figure 9:
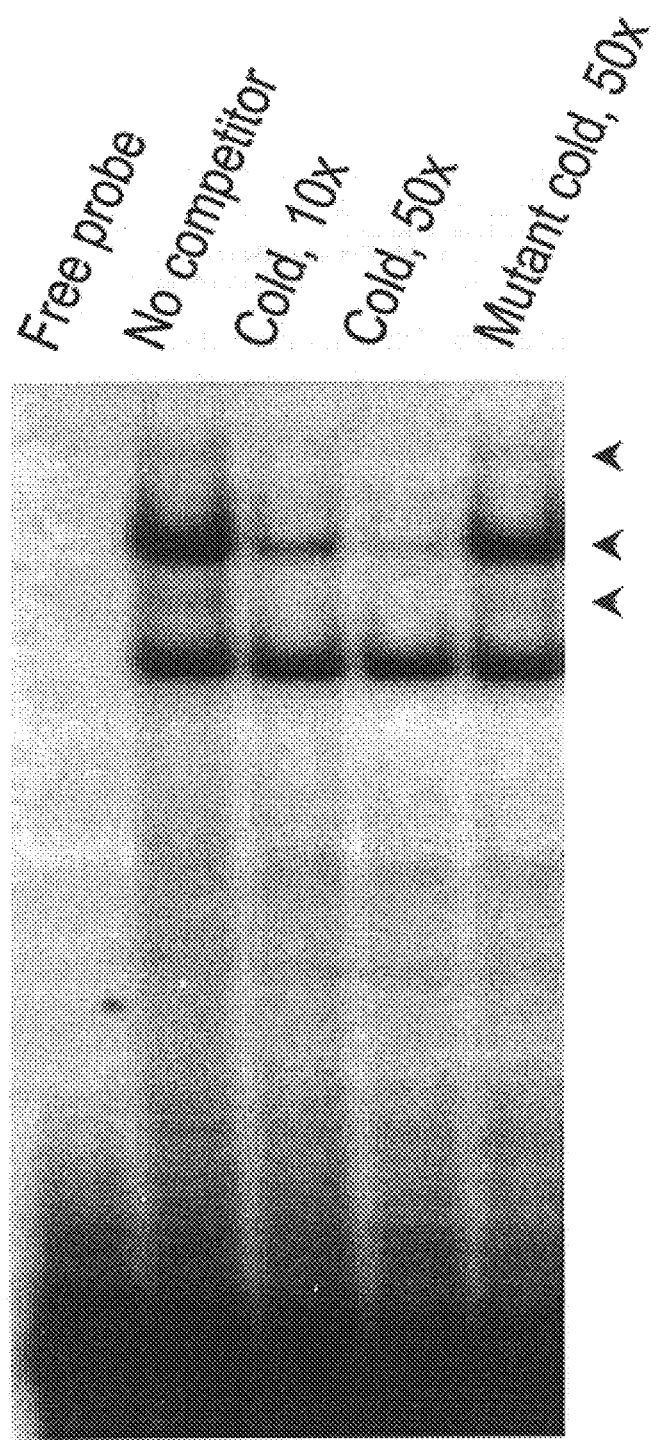
FIG. 9 shows the electrophoretic mobility shift assay. A radioactively labeled double-stranded DNA probe (28 bp) from the CHOP binding region of the promoter was incubated with Hep G2 whole cell extract and separated on a 5% polyacrylamide gel. To determine binding specificity unlabeled wild type and mutant probes were added as unlabeled competitors, as indicated above the corresponding lanes.

Electrophoretic DNA mobility shift assay was performed with a labeled probe spanning the promoter region −69 to −44, containing the putative CHOP binding site. First HepG2 whole cell extracts were prepared. HepG2 cells were grown in 100 mm dishes to 80–90% confluency and were scraped using buffer A (25 mM Tris-HCl, pH7.5; 50 mM KCl, 2 mM $MgCl_2$ 1 mM EDTA and 5 mM DTT) and pelleted by centrifugation. The cell pellet was resuspended in a small volume of buffer B (25 mM Tris-HCl, pH7.5; 0.42 M NaCl, 1.5 mM $MgCl_2$, 1 mM DTT, 0.5 mM EDTA, and 25% sucrose), forced 5 times through a 23-gauge needle and centrifuged for 3 min at 4° C. The supernatant was collected and frozen in several aliquots at −80° C. until needed (Timchenko et al., 1997). Two complementary primers (5'-AGGCGCGCGGTGCAATGTGGGCCAG-3'; SEQ ID NO:15 and 5'-AGGCTGGCCCAC-ATTGCACCGCGCG-3'; SEQ ID NO:16) at a concentration of 100 ng/µl in 2×SSC were annealed by heating to 85° C. and slow cooling to room temperature. The 3 bp AGG overhangs were filled with $^{32}p$ dCTP using Klenow enzyme according to standard procedures. The product was separated from dCTP on a G-25 spin column (5Prime-3Prime, Inc.). A 50–100,000 cpm aliquot of the probe was incubated for 20 min at room temperature with an aliquot of HepG2 whole cell extract containing 20–30 µg protein and 0.5 µg dI-dC (Pharmacia) in 20 mM Tris-HCl (pH 7.6), 100 mM KCl, 5 mM $MgCl_2$, 1 mM DTT, 10% glycerol in a total volume of 8 µl. Cold wild-type or mutant competitor (1 µl) were added in 10× or 50× excess molar concentrations to establish binding specificity. The reaction mixtures were resolved by electrophoresis on a 5% polyacrylamide gel. Incubation of this probe with HepG2 whole cell extract and subsequent separation of the DNA-protein adducts on a non-denaturing polyacrylamide gel showed one major and two minor bands (FIG. 9). These bands were specific as shown by their disappearance upon the addition of a 10- and 50-molar excess of cold unlabeled probe as competitor, but not with similar amounts of a cold mutant probe that was used in the transfection studies.

EXAMPLE 9

Demonstration of bidirectionality

As shown in Example 7, bidirectional activity of the aldehyde reductase promoter was demonstrated in the reporter gene assays by placing the promoter in both orientations in front of the firefly luciferase gene. Placement of fragments (−267 to +29; SEQ ID NO:23) and (−124 to +29; SEQ ID NO:24) in the reverse orientation in front of the firefly luciferase gene gave nearly identical or even higher expression of the luciferase reporter gene than in the forward orientation (FIG. 8). This finding shows that the aldehyde reductase gene possesses a bidirectional promoter activity.

To demonstrate that the aldehyde reductase promoter can drive expression of the two genes simultaneously, a construct that contained firefly and renilla luciferase genes in opposite orientations on both sides of the promoter was generated with methods well known in the art by inserting the renilla luciferase gene into a pGL3-basic vector that already had the (−124 to +29; SEQ ID NO:24) promoter fragment upstream of the firefly luciferase gene. Promoter activity was assessed in transient transfections and subsequent measurements of luciferase activities by dual-luciferase assays were performed as described in Example 7. Briefly, transient transfections were performed using the calcium phosphate precipitation method as described (Wang et al., 1993). For luciferase assay cells were divided into 24 well plates (6×$10^5$ cells per well) and transfected one day later with 0.24 pmol of DNA of the construct to be tested. Thirty eight fmol of pGL3-control vector which expresses firefly luciferase under control of the SV-40 promoter with enhancer were cotransfected with constructs containing renilla luciferase only to normalize for transfection efficiency. Firefly luciferase only constructs were cotransfected with 38 fmol pRL-TK vector. Dual-luciferase assays were carried out 48 hrs after transfection using the dual-luciferase kit made by Promega (Madison, Wis.). Cells were harvested using Passive Lysis Buffer, and 2–10 µl of cell extract was used to measure activity of the two luciferases separately in the same assay.

Figure 10:
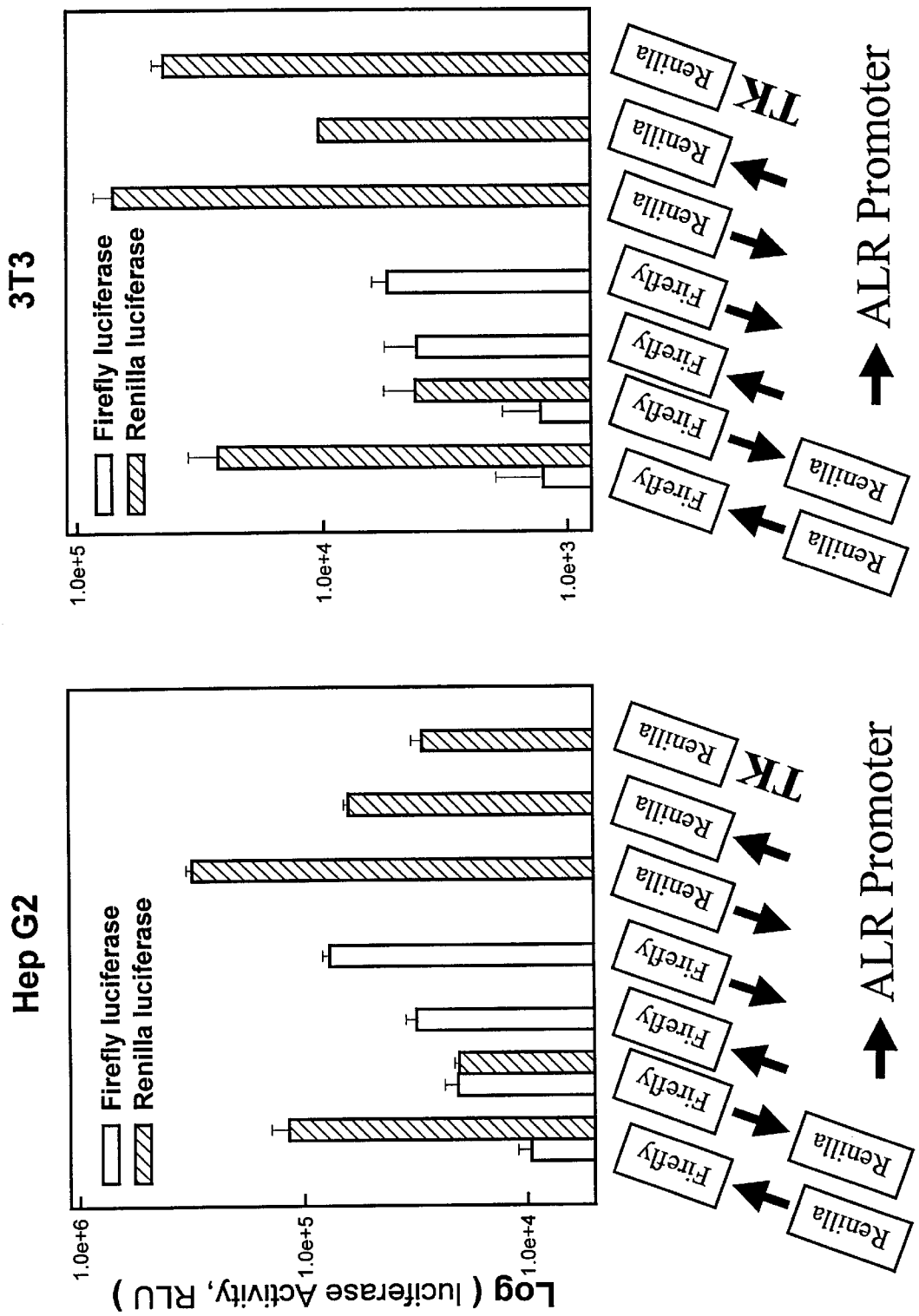
FIG. 10 demonstrates experiments performed in the dual luciferase assay for assessing promoter activity. In the legend, the arrow indicates (−124 to +29) (SEQ ID NO:24) fragment of the aldehyde reductase promoter, Firefly and Renilla in the boxes indicate firefly and renilla luciferase genes, respectively, and TK stands for TK-promoter in the pRL-TK vector.

FIG. 10 demonstrates luciferase activities observed in HepG2 and 3T3 cells where the arrow indicates the (−124 to +29; SEQ ID NO:24) promoter fragment and TK represents the thymidine kinase promoter. High levels of expression of both luciferases were achieved in cell lines from different organ origins, including liver (HepG2), kidney (293) and fibroblast (3T3) cell line. Reverse orientation of the promoter is 2–6-fold stronger than forward orientation in single or dual-gene constructs. In the orientation where the 3' end of the promoter fragment abuts renilla luciferase and the 5' end abuts firefly luciferase, expression of renilla and firefly luciferase genes is close to equimolar, demonstrating that it is possible to achieve equimolar expression of the two genes at high levels. The strength of the aldehyde reductase promoter is at the same order of magnitude as that of TK promoter (tested with firefly luciferase). These results demonstrate the ability of the aldehyde reductase promoter to drive expression of two genes simultaneously in different cell lines. Based on the ubiquitous tissue distribution of aldehyde reductase, the promoter is active in most tissues and cell lines. Expression levels of both luciferases exceed that obtained when renilla luciferase is expressed under the control of the TK promoter. Based on the ubiquitous tissue distribution of aldehyde reductase, it is expected that its promoter is active in most tissues and cell lines.

EXAMPLE 10

Expression of Thymidine Kinase and T-antigen

TK cDNA with bGH (growth hormone) poly-A signal was inserted in the StuI site of pS3 M-MLV (Moloney murine leukemia virus)-based retroviral plasmid (Faustinella et al., 1994) with its 3'-end closest to the 5'LTR of the vector. T-ag cDNA was PCR-amplified, digested with BamHI and SalI and inserted in the pS3TK plasmid in an orientation of the retroviral transcription. Finally, the (–124 to +85; SEQ ID NO:31) aldehyde reductase promoter fragment was inserted in the resulting pS3TKTag construct between TK and T-ag genes.

For TK and T-ag expression analysis Hep G2 cells in 60 mm plates were transfected with 10 µg DNA and harvested 72 hrs later for RNA. Total RNA was isolated using RNA-ZOL (Tel-Test, Inc.; Friendswood, Tex.) and 20 µg was loaded in each lane of the 1% agarose gel containing 18% formaldehyde. RNA was transferred onto a Nytran membrane (Schleicher and Schuell; Keene, N. H.) overnight using upward capillary method, and UV cross-linked to the membrane. Probes were labeled with 32P dCTP by nick-translation using a kit from Amersham (Piscataway, N.J.). The whole TK cDNA (1.2 kb) was used to detect TK. For T-ag, –700 bp 3' terminal fragment of T-ag cDNA was used as a probe. Hybridization was carried out using Ultrahyb buffer from Ambion (Austin, Tex.) according to the product protocol. Final wash was performed in 0.1×SSC, 0.1% SDS at 50° C., and the blot was visualized by autoradiography.

Figure 11:
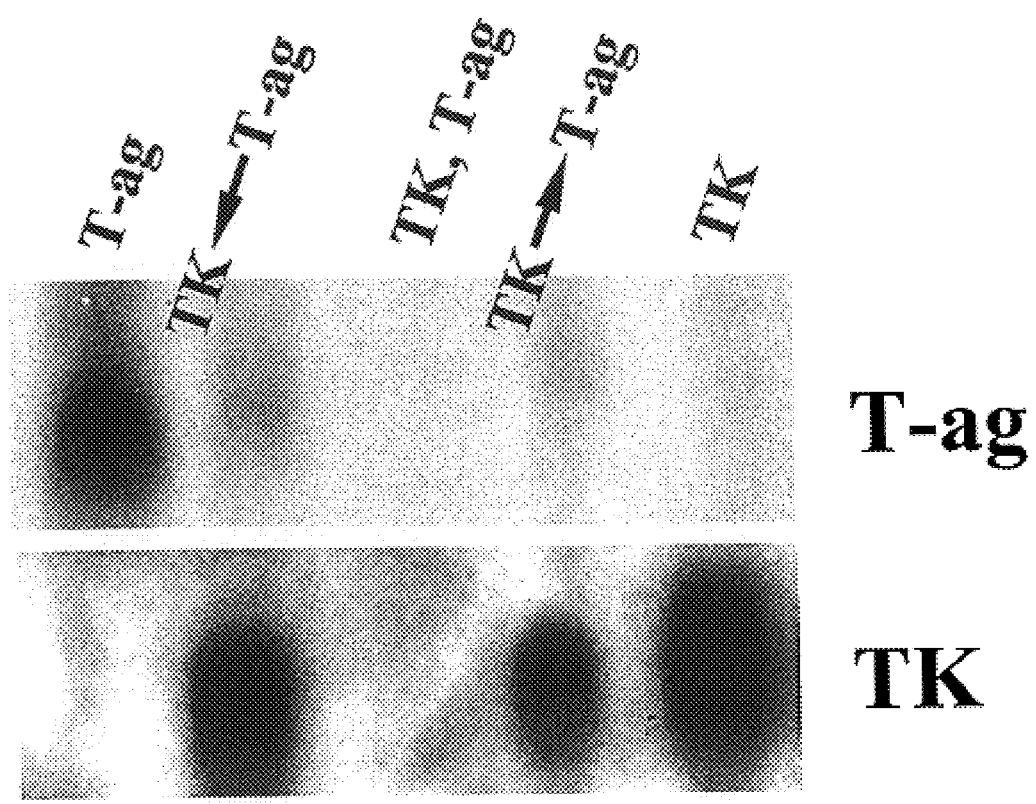
FIG. 11 depicts transient transfections of TK and T-antigen genes under the control of aldehyde reductase promoter fragment (−124 to +85) (SEQ ID NO:31) into Hep G2 cells.

Substantial expression of both genes is achieved 72 hrs after transfections of the retroviral construct containing TK and T-ag genes abutting aldehyde reductase promoter fragment (–124 to +85; SEQ ID NO:31) into Hep G2 cells, as shown by Northern blots (FIG. 11). The expression level of T-ag is comparable to that of T-ag expressing 293-T cell line, suggesting that the strength of the aldehyde reductase promoter is sufficient to express enough T-ag to cause the transformation of primary cells. TK gene is expressed at the same level as when placed under the control of the human elongation factor 1a (EF1a) promoter (Kim et al., 1990) that was used as a positive control. No TK or T-antigen transcripts are detected when cells are transfected with a construct that contains no promoter. Thus, TK and T-antigen expression is strong and driven by the aldehyde reductase promoter.

Figure 12:
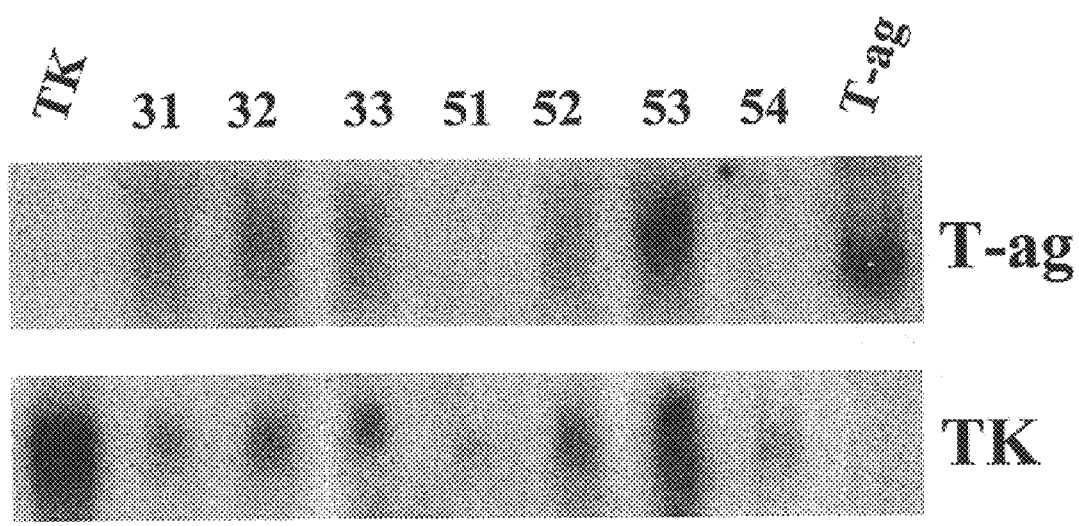
FIG. 12 shows analysis of TK and T-antigen expression in stable virus producing clones.

Stable clones of AM-12 cells expressing T-ag and TK under control of the aldehyde reductase promoter were generated. Constructs corresponding to the ones described above were generated in the pS3-lox vector containing loxP sites flanking the cloning cassette. These constructs were co-transfected with a neomycin containing plasmid into AM-12 retroviral packaging cell line using lipofectamine as per the manufacturer's directions (Life Technologies, Inc.; Gaithersburg, Md.). Stable clones were selected using G418 and were analyzed for TK and T-antigen expression by Northern blots (FIG. 12). Clone numbers starting with 3 have the 5' end of the promoter abutting T-ag, and numbers starting with 5 have the promoter in the opposite orientation. TK and T-ag are expressed at roughly the same level in both orientations of the promoter. Clone 53 expresses higher level of both genes than the other clones, which may be due to the higher metabolic rate of the cells of this clone (Groskreutz and Schenburn, 1997) or the integration site of the provirus. Both genes are expressed at substantial levels in transient and stable transfections in Hep G2 and AM-12 cell lines.

EXAMPLE 11

Significance of the Aldehyde Reductase Bidirectional Promoter

As presented herein, the aldehyde reductase promoter drives expression of a reporter gene when inserted in front of it in both forward and reverse orientations (Barski et al., 1999). Furthermore, characterization of a dual luciferase system allowed us to quantitatively compare the expression of two genes in both promoter orientations. It appears that the reverse orientation of the promoter is generally stronger than the forward one. The ratio of reverse:forward orientation for firefly luciferase appears to vary between 2 to 3, while the same ratio for renilla luciferase is 5 to 6. This difference may be due to interactions of the coding sequences with the promoter in specific orientation. Expression from the single gene constructs is 1.5–3 fold higher than from the dual-gene constructs. This may be due to the higher transfection efficiency for smaller single gene DNA, or might imply that only part of the promoter strength is used in each orientation in dual-gene constructs. In an orientation where Firefly luciferase is on the 5' while Renilla luciferase is on the 3' side of the promoter, approximately equimolar expression of both genes is achieved. This indicates that it is possible to achieve equimolar expression of the two genes of choice with the aldehyde reductase promoter. The same expression pattern was observed for several cell lines, which suggests there is predictability of the promoter action in respect to different organs and achieving expression in a wide range of tissues.

In a specific embodiment the aldehyde reductase promoter is used to create a system to assist in the controlled in vitro expansion of primary cells. In a further specific embodiment the cells are primary beta cells from the pancreas. Introduction of a specific tumoral antigen (SV-40 large T-antigen) to the primary cells allows them to grow in culture until T-antigen is excised using the Cre-lox system. Herpes simplex thymidine kinase (TK) is introduced together with T-antigen as a safety feature that allows destruction in the cells in which T-antigen was not excised, using pro-toxic drug ganciclovir before returning them to the patient (Kobayashi et al., 2000). Expression of both TK and T-antigen from the same promoter ensures that both of these genes are expressed in the same cells.

When inserted on both sides of the aldehyde reductase promoter TK and T-ag genes are expressed to a significant level in HepG2 and AM-12 cell lines in both promoter orientations. Stable clones were generated in a viral packaging cell line, AM-12, where the whole TK-ALR promoter-T-ag assembly was inserted into the provirus. These clones not only express TK and T-ag, but have the potential to produce retrovirus in order to deliver TK-T-ag expression cassette into other cells.

In addition to the expression of these genes both in transient and stable transfections, viral RNA is also detected in the supernatant of the retrovirus producing cells (AM-12). Thus, presence of an active bidirectional promoter inside the provirus does not prevent viral RNA expression from 5'-LTR retroviral promoter and virus assembly and production. These data demonstrate that the bidirectional promoter can be used in a retroviral context to express two genes of interest for gene therapy.

Thus, as described herein, there is a novel aldehyde reductase bidirectional promoter for use in the simultaneous expression of any two nucleic acids in a variety of mammalian cells. The Examples provided demonstrate analysis and comparisons of the strength of this promoter in both orientations using two luciferase genes, and demonstrated practical usefulness of the promoter by expressing two genes useful for gene therapy in a retroviral context.

The major advantages of the aldehyde reductase promoter are summarized below:

1. Simultaneous expression of two proteins or subunits of the same protein at the similar levels is possible.
2. Aldehyde reductase promoter is active in many tissues, since its gene product—aldehyde reductase, is present in every human tissue with the highest levels found in kidney, liver and thyroid. Thus, it allows the flexibility in achieving expression in the desirable tissue or multiple tissues.
3. Strong expression can be obtained. Its activity is comparable with an SV-40 promoter and enhancer or HSV-TK promoter.
4. Endogenous cellular promoter has a potential to remain active for a long period of time in contrast to extensively used viral promoters that tend to be shut down in vivo (Loser et al., 1998; Xu et al., 1989; Duch et al., 1994).
5. Substantial space saving using one promoter to direct expression of two transcripts may be desirable for ease of vector production.

A skilled artisan has available vast resources in molecular biology and related fields, such as Sambrook et al. (1988) and Ausubel et al. (1994), to clone any desirable nucleic acid in the forward and/or reverse orientation of the bidirectional promoter sequences presented herein. Furthermore, a skilled artisan has quick and easy access to databases such as GenBank to readily ascertain a desirable sequence in order to utilize the present invention. A skilled artisan would know how to manipulate the present invention to achieve a desirable result, including equimolar expression of two gene products, such as inclusion or omission of a nucleic acid segment which facilitates the desirable result. For example, a skilled artisan may reduce the size of a nucleic acid to be expressed to improve transfection efficiency or change the orientation of the nucleic acid, relative to the promoter sequence. Another adjustment may include utilization of an alternate sequence as being utilized, such as another sequence selected from SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29, SEQ ID NO:30 and/or SEQ ID NO:31.

A skilled artisan would know how to select a sequence to be expressed based on a desired result or application, but some examples of sequences other than the reporter sequences described herein include ras, myc, raf, erb, src, fms, jun, trk, ret, gsp, hst, bcl abl, Rb, CFTR, p16, p21, p27, p53, p57, p73, C-CAM, APC, CTS-1, zacl, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF and thymidine kinase.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

PATENTS

U.S. Pat. No. 5,840,873, issued Nov. 24, 1998
U.S. Pat. No. 5,843,640, issued Dec. 1, 1998
U.S. Pat. No. 5,843,650, issued Dec. 1. 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,993, issued Dec. 29, 1998
U.S. Pat. No. 5,853,992, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999

Eur opean Application No. 32 0 308
Eur opean Application No. 3 29 822
GB Application No. 2 202 328
PCT Application No. PCT/US87/00880
PCT Application No. PCT/US89/01025
PCT Application WO 88/10315
PCT Application WO 89/06700

PUBLICATIONS

Ausubel, F. M., et al. (1994). *Current Protocols in Molecular Biology*, John Wiley & Sons, Inc.

Bachur, N. R. (1976). Cytoplasmic aldo-keto reductases: a class of drug metabolizing enzymes. Science 193, 595–597.

Bagnasco, S. M., Uchida, S., Balaban, R. S., Kador, P. F. & Burg, M. B. (1987). Induction of aldose reductase and sorbitol in renal inner medullary cells by elevated extracellular NaCl. *Proc Natl Acad Sci U S A* 84: 1718–1720.

Barski, O. A., Gabbay, K. H. & Bohren, K. M. (1996a). Aldehyde Reductase: Catalytic Mechanism and Substrate Recognition. In "Enzymology and Molecular Biology of Carbonyl Metabolism 6" (Weiner, e.al., ed.), pp. 443–451, Plenum Press, New York Barski, O. A., Gabbay, K. H. & Bohren, K. M. (1996b). The C-terminal loop of aldehyde reductase determines the substrate and inhibitor specificity. Biochemistry 35: 14276–14280.

Barski, O. A., Gabbay, K. H., Grimshaw, C. E. & Bohren, K. M. (1995). Mechanism of human aldehyde reductase: characterization of the active site pocket. *Biochemistry* 34: 11264–11275.

Barski, O. A., Gabbay, K. H., and Bohren, K. M. (1999). Characterization of the human aldehyde reductase gene and promoter. *Genomics* 60, 188–198.

Belsham, G. J. and Sonenberg, N. (1996). RNA-protein interactions in regulation of picornavirus RNA translation. Microbiol Rev 60, 499–511.

Bennett, M. J., Schlegel, B. P., Jez, J. M., Penning, T. M. & Lewis, M. (1996). Structure of 3 alpha-hydroxysteroid/dihydrodiol dehydrogenase complexed with NADP+. *Biochemistry* 35: 10702–10711.

Bohren, K. M., Bullock, B., Werrnuth, B. & Gabbay, K. H. (1989). The aldo-keto reductase superfamily. cDNAs and deduced amino acid sequences of human aldehyde and aldose reductases. *J Biol Chem* 264: 9547–9551.

Bohren, K. M., Grimshaw, C. E., Lai, C. J., Harrison, D. H., Ringe, D., Petsko, G. A. & Gabbay, K. H. (1994). Tyrosine-48 is the proton donor and histidine-110 directs substrate stereochemical selectivity in the reduction reaction of human aldose reductase: enzyme kinetics and crystal structure of the Y48H mutant enzyme. *Biochemistry* 33: 2021–2032.

Bruce, N. C., Willey, D. L., Coulson, A. F. & Jeffery, J. (1994). Bacterial morphine dehydrogenase further defines a distinct superfamily of oxidoreductases with diverse functional activities. *Biochem J* 299: 805–811.

Chabot, B. (1996). Directing alternative splicing: cast and scenarios. *Trends Genet* 12: 472–478.

Crozat, A., Aman, P., Mandahl, N. & Ron, D. (1993). Fusion of CHOP to a novel RNA-binding protein in human myxoid liposarcoma. *Nature* 363: 640–644.

Duch, M., Paludan, K., Jorgensen, P., and Pedersen, F. S. (1994). Lack of correlation between basal expression levels and susceptibility to transcriptional shutdown among single-gene murine leukemia virus vector proviruses. J Virol 68, 5596–5601.

el-Kabbani, O., Judge, K., Ginell, S. L., Myles, D. A., DeLucas, L. J. & Flynn, T. G. (1995). Structure of porcine aldehyde reductase holoenzyme. *Nat Struct Biol* 2: 687–692.

Faustinella, F., Kwon, H., Serrano, F., Belmont, J. W., Caskey, C. T., and Aguilar-Cordova, E. (1994). A new family of murine retroviral vectors with extended multiple cloning sites for gene insertion. Hum Gene Ther 5, 307–312.

Feather, M. S., Flynn, T. G., Munro, K. A., Kubiseski, T. J., and Walton, D. J. (1995). Catalysis of reduction of carbohydrate 2-oxoaldehydes (osones) by mammalian aldose reductase and aldehyde reductase. Biochim Biophys Acta 1244, 10–16.

Fornace, A. J. J., Nebert, D. W., Hollander, M. C., Luethy, J. D., Papathanasiou, M., Fargnoli, J. & Holbrook, N. J. (1989). Mammalian genes coordinately regulated by growth arrest signals and DNA- damaging agents. *Mol Cell Biol* 9: 4196–4203.

Gabbay, K. H. & Cathcart, E. S. (1974). Purification and immunologic identification of aldose reductases. Diabetes 23: 460–468. Wisconsin Package. Genetics Computer Group (9.1): Madison, Wis.: Oxford Molecular Group, Inc. (1998)

Graham, A., Brown, L., Hedge, P. J., Gammack, A. J. & Markham, A. F. (1991). Structure of the human aldose reductase gene. *J Biol Chem* 266: 6872–6877.

Groskreutz, D. J. and Schenburn, E. T. (1997). Reporter Systems. In Methods in Molecular Biology 63. R. S. Tuan, ed. (Totowa).

Harrison, D. H., Bohren, K. M., Ringe, D., Petsko, G. A. & Gabbay, K. H. (1994). An anion binding site in human aldose reductase: mechanistic implications for the binding of citrate, cacodylate, and glucose 6-phosphate. *Biochemistry* 33: 2011–2020.

Jang, S. K., Davies, M. V., Kaufman, R. J., and Wimmer, E. (1989). Initiation of protein synthesis by internal entry of ribosomes into the 5' nontranslated region of encephalomyocarditis virus RNA in vivo. J Virol 63, 1651–1660.

Jang, S. K., Pestova, T. V., Hellen, C. U., Witherell, G. W., and Wimmer, E. (1990). Cap-independent translation of picornavirus RNAs: structure and function of the internal ribosomal entry site. Enzyme 44, 292–309.

Johnson, P. & Friedmann, T. (1990). Limited bidirectional activity of two housekeeping gene promoters: human HPRT and PGK. *Gene* 88: 207–213.

Ju, G., Boone, L., and Skalka, A.M. (1980). Isolation and characterization of recombinant DNA clones of avian retroviruses: size heterogeneity and instability of the direct repeat. J Virol 33, 1026–1033.

Junker, U., Bohnlein, E., and Veres, G. (1995). Genetic instability of a MoMLV-based antisense double-copy retroviral vector designed for HIV-1 gene therapy. Gene Ther 2, 639–646.

Khanna, M., Qin, K. N., Wang, R. W. & Cheng, K. C. (1995). Substrate specificity, gene structure, and tissue-specific distribution of multiple human 3 alpha-hydroxysteroid dehydrogenases. *J Biol Chem* 270: 20162–20168.

Kim, D. W., Uetsuki, T., Kaziro, Y., Yamaguchi, N., and Sugano, S. (1990). Use of the human elongation factor 1 alpha promoter as a versatile and efficient expression system. Gene 91, 217–223.

Ko, B. B., Ruepp, B., Bohren, K. M., Gabbay, K. H. & Chung, S. S. (1997). Identification and characterization of multiple osmotic response sequences in the human aldose reductase gene. *J Biol Chem* 272: 16431–16437.

Kobayashi, N., Fujiwara, T., Westerman, K. A., Inoue, Y., Sakaguchi, M., Noguchi, H., Miyazaki, M., Cai, J., Tanaka, N., Fox, I. J., and Leboulch, P. (2000). Prevention of acute liver failure in rats with reversibly immortalized human hepatocytes [see comments]. Science 287, 1258–1262.

Koller, E., Hayman, A. R. & Trueb, B. (1991). The promoter of the chicken alpha 2(VI) collagen gene has features characteristic of house-keeping genes and of proto-oncogenes. *Nucleic Acids Res* 19: 485–491.

Loser, P., Jennings, G. S., Strauss, M., and Sandig, V. (1998). Reactivation of the previously silenced cytomegalovirus major immediate-early promoter in the mouse liver: involvement of NFkappaB. J Virol 72, 180–190.

Lou, H., Hammond, L., Sharma, V., Sparkes, R. S., Lusis, A. J. & Stolz, A. (1994). Genomic organization and chromosomal localization of a novel human hepatic dihydrodiol dehydrogenase with high affinity bile acid binding. *J Biol Chem* 269: 8416–8422.

Mano, Y., Suzuki, K., Yamada, K.a.S.N. & . (1961). Enzymatic studies on TPN-L-hexonate dehydrogenase from rat liver. *J Biochem* 49: 618–634.

Molowa, D. T., Shayne, A. G. & Guzelian, P. S. (1986a). Purification and characterization of chlordecone reductase from human liver. *J Biol Chem* 261: 12624–12627.

Molowa, D. T., Wrighton, S. A., Blanke, R. V. & Guzelian, P. S. (1986b). Characterization of a unique aldo-keto reductase responsible for the reduction of chlordecone in the liver of the gerbil and man. *J Toxicol Environ Health* 17: 375–384.

Qin, K. N., Khanna, M. & Cheng, K. C. (1994). Structure of a gene coding for human dihydrodiol dehydrogenase/bile acid-binding protein. *Gene* 149: 357–361.

Quandt, K., Frech, K., Karas, H., Wingender, E. & Werner, T. (1995). MatInd and MatInspector: new fast and versatile tools for detection of consensus matches in nucleotide sequence data. *Nucleic Acids Res* 23: 4878–4884.

Rabbitts, T. H., Forster, A., Larson, R. & Nathan, P. (1993). Fusion of the dominant negative transcription regulator CHOP with a novel gene FUS by translocation t(12;16) in malignant liposarcoma. *Nat Genet* 4: 175–180.

Ron, D. & Habener, J. F. (1992). CHOP, a novel developmentally regulated nuclear protein that dimerizes with transcription factors C/EBP and LAP and functions as a dominant-negative inhibitor of gene transcription. *Genes Dev* 6: 439–453.

Rondeau, J. M., Tete-Favier, F., Podjarny, A., Reymann, J. M., Barth, P., Biellmann, J. F. & Moras, D. (1992). Novel NADPH-binding domain revealed by the crystal structure of aldose reductase. *Nature* 355: 469–472.

Sambrook, Fritsch, Maniatis, In: Molecular Cloning: A Laboratory Manual, Vol. 1, Cold Spring Harbor Laboratory Press, Cold Spring Harbor, N.Y., Ch. 7,7.19–17.29, 1989.

Stapleton, G., Somma, M. P. & Lavia, P. (1993). Cell type-specific interactions of transcription factors with a housekeeping promoter in vivo. *Nucleic Acids Res* 21: 2465–2471.

Suzuki, K., Koh, Y. H., Mizuno, H., Hamaoka, R., and Taniguchi, N. (1998). Overexpression of aldehyde reductase protects PC12 cells from the cytotoxicity of methylglyoxal or 3-deoxyglucosone. J Biochem (Tokyo) 123, 353–357.

Timchenko, N. A., Harris, T. E., Wilde, M., Bilyeu, T. A., Burgess-Beusse, B.L., Finegold, M. J. & Darlington, G. J. (1997). CCAAT/enhancer binding protein alpha regulates p21 protein and hepatocyte proliferation in newborn mice. *Mol Cell Biol* 17: 7353–7361.

Tipton, K. F., Houslay, M. D. & Turner, A. J. (1977). Metabolism of aldehydes in brain. *Essays Neurochem Neuropharmacol* 1: 103–138.

Turner, A. J., Illingworth, J. A. & Tipton, K. F. (1974). Simulation of biogenic amine metabolism in the brain. *Biochem J* 144: 353–360.

Ubeda, M., Wang, X. Z., Zinszner, H., Wu, I., Habener, J. F. & Ron, D. (1996a). Stress-induced binding of the transcriptional factor CHOP to a novel DNA control element. *Mol Cell Biol* 16: 1479–1489.

Ubeda, M., Wang, X. Z., Zinszner, H., Wu, I., Habener, J. F. & Ron, D. (1996b). Stress-induced binding of the transcriptional factor CHOP to a novel DNA control element. *Mol Cell Biol* 16: 1479–1489.

Wang, K., Bohren, K. M. & Gabbay, K. H. (1993). Characterization of the human aldose reductase gene promoter. *J Biol Chem* 268: 16052–16058.

Wermuth, B. & Monder, C. (1983). Aldose and aldehyde reductase exhibit isocorticosteroid reductase activity. *Eur J Biochem* 131: 423–426.

Wermuth, B., Munch, J. D. & von Wartburg, J. P. (1977). Purification and properties of NADPH-dependent aldehyde reductase from human liver. *J Biol Chem* 252: 3821–3828.

Wilson, D. K., Bohren, K. M., Gabbay, K. H. & Quiocho, F. A. (1992). An unlikely sugar substrate site in the 1.65 A structure of the human aldose reductase holoenzyme implicated in diabetic complications. *Science* 257: 81–84.

Wilson, D. K., Nakano, T., Petrash, J. M. & Quiocho, F. A. (1995). 1.7 A structure of FR-1, a fibroblast growth factor-induced member of the aldo-keto reductase family, complexed with coenzyme and inhibitor. *Biochemistry* 34: 14323–14330.

Wirth, H. P. & Wermuth, B. (1985). Immunohistochemical localisation of aldehyde and aldose reductase in human tissues. *Prog Clin Biol Res* 174: 231–239.

Xu, C. F., Chambers, J. A. & Solomon, E. (1997). Complex regulation of the BRCA1 gene. *J Biol Chem* 272: 20994–20997.

Zinszner, H., Kuroda, M., Wang, X., Batchvarova, N., Lightfoot, R. T., Remotti, H., Stevens, J. L. & Ron, D. (1998). CHOP is implicated in programmed cell death in response to impaired function of the endoplasmic reticulum. *Genes Dev* 12: 982–995.

One skilled in the art readily appreciates that the present invention is well adapted to carry out the objectives and obtain the ends and advantages mentioned as well as those inherent therein. Sequences, promoters, systems, pharmaceutical compositions, treatments, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

What is claimed:

1. A DNA sequence of the formula selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29, SEQ ID NO:30, and SEQ ID NO:31, or fragments thereof; wherein said fragments function as bidirectional promoters.

2. A promoter having the characteristic of promoting transcription of two separate nucleotide sequences, wherein one of such nucleotide sequences is operatively linked to the 5' end of said promoter sequence and is transcribed 5' to 3' in the direction opposite from the 5' to 3' direction of said promoter sequence and the other of such nucleotide sequences is operatively linked to the 3' end of said promoter sequence and is transcribed 5' to 3' in the same direction as the 5' to 3' direction of said promoter sequence, wherein the promoter promotes transcription of the two nucleotide sequences in approximately equimolar amounts, and wherein the promoter sequence is selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30, SEQ ID NO:31 and fragments thereof wherein said fragments function as bidirectional promoters.

3. A recombinant DNA vector comprising:
the promoter sequence selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31 or fragments thereof, wherein said fragments function as a bidirectional promoter; a first DNA sequence encoding a gene operatively linked to the 5' end of the promoter sequence wherein when said first DNA sequence is transcribed it is transcribed 5' to 3' in the direction opposite from the 5' to 3' direction of the promoter sequence; and a second DNA sequence encoding a gene operatively linked to the 3' end of the promoter sequence wherein when said second DNA sequence is transcribed it is transcribed 5' to 3' in the same direction as the 5' to 3' direction of the promoter sequence.

4. The recombinant DNA vector of claim 3, wherein said first DNA sequence and said second DNA sequence encode nonidentical nucleotide sequences.

5. The recombinant DNA vector of claim 3, wherein one of said DNA sequences encodes a reporter sequence.

6. The recombinant DNA vector of claim 5, wherein the reporter sequence is selected from the group consisting of ampicillin, neomycin, kanamycin, luciferase, β-galactosidase, β-glucuronidase, chloramphenicol acetyltransferase (CAT), blue fluorescent protein (BFP), green fluorescent protein (GFP), and placental alkaline phosphatase.

7. The recombinant DNA vector of claim 3, wherein one of the DNA sequences encodes a heavy chain of an antibody and the other DNA sequence encodes a light chain of said antibody.

8. The method of preparing an antibody containing a light chain and a heavy chain of said antibody wherein said light and heavy chains are encoded for by the DNA sequences in the recombinant DNA vector of claim 7 comprising:
(a) expression of said DNA sequences, wherein said heavy and light chain sequences combine to form an antibody; and
(b) recovering the formed antibody.

9. The recombinant DNA vector of claim 3, wherein one DNA sequence encodes the p35 subunit of Interleukin-12 and the other DNA sequence encodes the p40 subunit of Interleukin-12.

10. A method of preparing Interleukin-12 containing p35 and p40 subunits of said Interleukin-12 wherein said p35 and p40 subunits are encoded for by the DNA sequences in the recombinant DNA vector of claim 9 comprising:
(a) expression of said DNA sequences, wherein said subunit sequences combine to form Interleukin-12; and
(b) recovering the formed Interleukin-12.

11. The recombinant DNA vector of claim 3, wherein one DNA sequence encodes a subunit of Interleukin-2 and the other DNA sequence encodes the other subunit of Interleukin-2.

12. A method of preparing Interleukin-2 containing subunits of said Interleukin-2 wherein said subunits are encoded for by the DNA sequences in the recombinant DNA vector of claim 11 comprising:
(a) expression of said DNA sequences, wherein said subunit sequences combine to form Interleukin-2; and
(b) recovering the formed Interleukin-2.

13. The recombinant DNA vector of claim 3 wherein said DNA sequences each encode growth hormone receptor subunits.

14. A method of preparing the growth hormone receptor containing the subunits of said growth hormone receptor wherein said subunits are encoded for by the DNA sequences in the recombinant DNA vector of claim 13 comprising:
  (a) expression of said DNA sequences, wherein said subunit sequences combine to form a growth hormone receptor; and
  (b) recovering the formed growth hormone receptor.

15. The recombinant DNA vector of claim 3 wherein at least one of said DNA sequences encodes a subunit of a homodimer.

16. A method of preparing a homodimer containing the subunit of said homodimer wherein said subunit is encoded for by the DNA sequences in the recombinant DNA vector of claim 15 comprising:
  (a) expression of said DNA sequences, wherein said subunit sequences combine to form a homodimer; and
  (b) recovering the formed homodimer.

17. The recombinant DNA vector of claim 3 wherein one DNA sequence encodes one subunit of a heterodimer and the other DNA sequence encodes another subunit of said heterodimer.

18. A method of preparing a heterodimer containing the subunits of said heterodimer wherein said subunits are encoded for by the DNA sequences in the recombinant DNA vector of claim 17 comprising:
  (a) expression of said DNA sequences, wherein said subunit sequences combine to form a heterodimer; and
  (b) recovering the formed heterodimer.

19. The recombinant DNA vector of claim 3 wherein at least one nucleotide sequence encodes a RNA; said RNA being the final product of said nucleotide sequence.

20. The recombinant DNA vector of claim 19 wherein said RNA is selected from the group comsisting of telomerase RNA, snRNA, snoRNA, scRNA, antisence RNA and XIST RNA.

21. The method of preparing a ribonucleoprotein containing an RNA and a protein each encoded by one of the DNA sequences of the recombinant DNA vector of claim 3 comprising:
  (a) expression of said DNA sequences, wherein said RNA and protein sequences combine to form a ribonucleoprotein; and
  (b) recovering the formed ribonucleoprotein.

22. A recombinant DNA vector comprising:
  the promoter sequence selected from the group consisting of SEQ ID NO:19, SEQ ID NO:20, SEQ ID NO:22, SEQ ID NO:23, SEQ ID NO:24, SEQ ID NO:25, SEQ ID NO:26, SEQ ID NO:27, SEQ ID NO:29; SEQ ID NO:30 and SEQ ID NO:31 or fragments thereof, wherein said fragments function as a bidirectional promoter; a first polylinker site into which a first DNA sequence is operatively linked to the 5' end of the promoter sequence, wherein when said first DNA sequence is transcribed it is transcribed 5' to 3' in the direction opposite from the 5' to 3' direction of the promoter sequence; and a second polylinker site into which a second DNA sequence encoding a gene operatively linked to the 3' end of the promoter sequence wherein when said second DNA sequence is transcribed it is transcribed 5' to 3' in the same direction as the 5' to 3' direction of the promoter sequence.

23. The recombinant DNA vector of claim 3, wherein said vector further comprises a cassette, wherein said cassette comprises one DNA sequence which encodes a suicide nucleic acid sequence and the other DNA sequence which encodes an immortalization nucleic acid sequence, wherein both DNA sequences are transcribed from the promoter sequence.

24. The vector of claim 23, wherein said suicide nucleic acid sequence is thymidine kinase (TK).

25. The vector of claim 23, wherein said immortalization nucleic acid sequence is selected from the group consisting of T-antigen, telomerase catalytic protein subunit and myc.

26. A method to initiate proliferation of a cell comprising the step of introducing the vector of claim 23 into said cell under conditions wherein activation of the bidirectional promoter to transcribe said immortalization nucleic acid sequence in said cell initiates proliferation of said cell.

27. The recombinant DNA vector of claim 23, wherein said vector further comprises excision sites flanking said cassette, wherein said excision sites are selected from the group consisting of lox, FLP recognition target sites, restriction endonuclease sites, and transposon sequences.

28. A method to initiate proliferation of a cell comprising the step of introducing the vector of claim 27 into said cell under conditions wherein activation of the bidirectional promoter to transcribe said immortalization nucleic acid sequence in said cell initiates proliferation of said cell.

29. The method of claim 26 or 28, wherein said primary cell is selected from the group consisting of insulin-producing beta cell and liver cell.

30. The method of claim 26 or 28, wherein said cell is a primary cell.

31. The method of claim 28, wherein said introduction step further comprises integration of said excision sites and said cassette into a provirus of said cell.

32. The method of claim 31, wherein said method further comprises excising said immortalization nucleic acid sequence from said provirus through said excision sites.

33. The method of claim 32, wherein said method further comprises destroying a cell which has failed to excise said immortalization nucleic acid sequence.

34. The recombinant DNA vector of claim 3 or 22 further comprising a poly A+ polyadenylation sequence operatively linked to the 3' end of at least one of said first or second DNA sequences.

* * * * *

SEQUENCE LISTING

<160> NUMBER OF SEQ ID NOS: 31

<210> SEQ ID NO 1
<211> LENGTH: 108
<212> TYPE: DNA
<213> ORGANISM: Human

<400> SEQUENCE: 1

| agccagaaat gtgaagtgct agctgaagga tgagcagcag ctagccaggc aaaggcagaa | 60 |
| ctgagcccag gccacagtac cctattcacg ctctgtgctt gtgccaag | 108 |

<210> SEQ ID NO 2
<211> LENGTH: 52
<212> TYPE: DNA
<213> ORGANISM: Human

<400> SEQUENCE: 2

| ggggcaatgg cggcttcctg tgttctgggg caatggcggc ttcctgtgtt ct | 52 |

<210> SEQ ID NO 3
<211> LENGTH: 510
<212> TYPE: DNA
<213> ORGANISM: Human

<400> SEQUENCE: 3

| taaaaccatg tttattaagt gttaagcaca gtgcctggca cataacgtgc tgggcggggt | 60 |
| ctatggtcca gacaggggga ccaggcactt tccagcgcct ggatctgcag acgcgaggtc | 120 |
| ttctgtattc tggccaatct tggtgttgca gctgctctct gggcctcagt ttgcttgaac | 180 |
| taaatgtaac ggggccaact taggtgaact ttgggaatcc agccaacctg actttaggga | 240 |
| gagtatggag ccacggatgg cattgtgaat ccggagggcc acaccagaa gaacctgcaa | 300 |
| cgtggcatct gctaccttac ttcccccgga aaagcgcctg cggcggcgcc taggcgcgcg | 360 |
| gtgcaatgtg ggccagcaaa aggcgaggct ggccccgccc cttgcaccgc ccacgtggcc | 420 |
| agcgccacct gcctcattgt gcccaggagt tctccaaacc cgcgctgcgg agtgagtgac | 480 |
| caagttccgg ccagttcgac ctcgaggatc | 510 |

<210> SEQ ID NO 4
<211> LENGTH: 4
<212> TYPE: DNA
<213> ORGANISM: Human

<400> SEQUENCE: 4

| cata | 4 |

<210> SEQ ID NO 5
<211> LENGTH: 25
<212> TYPE: DNA
<213> ORGANISM: Human

<400> SEQUENCE: 5

| gatggaaaac agagctggga ggtag | 25 |

<210> SEQ ID NO 6
<211> LENGTH: 23
<212> TYPE: DNA
<213> ORGANISM: Human

<400> SEQUENCE: 6

-continued ggtgagacca cgtgctcatg gct                                              23

<210> SEQ ID NO 7
<211> LENGTH: 24
<212> TYPE: DNA
<213> ORGANISM: Human

<400> SEQUENCE: 7
gcatgccaag ctgaggagct tgac                                             24

<210> SEQ ID NO 8
<211> LENGTH: 26
<212> TYPE: DNA
<213> ORGANISM: Human

<400> SEQUENCE: 8
tattcacgct ctgtgcttgt gccaag                                           26

<210> SEQ ID NO 9
<211> LENGTH: 22
<212> TYPE: DNA
<213> ORGANISM: Human

<400> SEQUENCE: 9
agcagcagct agccaggcaa ag                                               22

<210> SEQ ID NO 10
<211> LENGTH: 26
<212> TYPE: DNA
<213> ORGANISM: Human

<400> SEQUENCE: 10
tattcacgct ctgtgcttgt gccaag                                           26

<210> SEQ ID NO 11
<211> LENGTH: 23
<212> TYPE: DNA
<213> ORGANISM: Human

<400> SEQUENCE: 11
agtagaacac aggaagccgc cat                                              23

<210> SEQ ID NO 12
<211> LENGTH: 31
<212> TYPE: DNA
<213> ORGANISM: Human

<400> SEQUENCE: 12
tgaccaggct cactcttcca ggtacccaga c                                     31

<210> SEQ ID NO 13
<211> LENGTH: 28
<212> TYPE: DNA
<213> ORGANISM: Human

<400> SEQUENCE: 13
ctcaccgcta gacttaagct gaggatcg                                         28

<210> SEQ ID NO 14
<211> LENGTH: 24
<212> TYPE: DNA
<213> ORGANISM: Human

-continued

```
<400> SEQUENCE: 14
aatcagaggc atcttctgcc cagt                                            24

<210> SEQ ID NO 15
<211> LENGTH: 25
<212> TYPE: DNA
<213> ORGANISM: Human

<400> SEQUENCE: 15
aggcgcgcgg tgcaatgtgg gccag                                           25

<210> SEQ ID NO 16
<211> LENGTH: 25
<212> TYPE: DNA
<213> ORGANISM: Human

<400> SEQUENCE: 16
aggctggccc acattgcacc gcgcg                                           25

<210> SEQ ID NO 17
<211> LENGTH: 1196
<212> TYPE: DNA
<213> ORGANISM: Human

<400> SEQUENCE: 17
gggtggaact tccccctcac cgccagactt aagctgagga tcgttggatc tctggcgggg     60
tgcagaactg agcccaggcc acagtaccct attcacgctc tgtgcttgtg ccaaggggc     120 aatggcggct tcctgtgttc tactgcacac tgggcagaag atgcctctga ttggtctggg    180
tacctggaag agtgagcctg gtcaggtaaa agcagctgtt aagtatgccc ttagcgtagg    240
ctaccgccac attgattgtg ctgctatcta cggcaatgag cctgagattg gggaggccct    300
gaaggaggac gtgggaccag caaggcggt gcctcgggag gagctgtttg tgacatccaa     360
gctgtggaac accaagcacc accccgagga tgtggagcct gccctccgga agactctggc    420
tgacctccag ctggagtatc tggacctgta cctgatgcac tggccttatg cctttgagcg    480
gggagacaac cccttcccca agaatgctga tgggactata tgctacgact ccacccacta    540
caaggagact tggaaggctc tggaggcact ggtggctaag gggctggtgc aggcgctggg    600
cctgtccaac ttcaacagtc ggcagattat gacatactca gtgtggcctc cgtgcgtcca    660
gctgtcttgc aggtggaatg ccacccatac ttggctcaaa atgagctaat tgcccactgc    720
caagcacgtg gcttggaggt aactgcttat agccctttgg gctcctctga tcgtgcatgg    780
cgtgatcctg atgagcctgt cctgctggag gaaccagtag tcctggcatt ggctgaaaag    840
tatggccgat ctccagctca gatcttgctc aggtggcagg tccagcggaa agtgatctgc    900
atccccaaaa gtatcactcc ttctcgaatc cttcagaaca tcaaggtgtt tgacttcacc    960
tttagcccag aagagatgaa gcagctaaat gccctgaaca aaaattggag atatattgtg   1020
cctatgctta cggtggatgg gaagagagtc ccaaggggatg cagggcatcc tctgtaccccc  1080 tttaatgacc cgtactgaga ccacagcttc ttggcctccc ttccagctct gcagctaatg   1140
aggtcctgcc acaacggaaa gagggagtta ataaagccat ggagcatcc ataaaa        1196

<210> SEQ ID NO 18
<211> LENGTH: 1132
<212> TYPE: DNA
<213> ORGANISM: Human

<400> SEQUENCE: 18
```

```
agccagaaat gtgaagtgct agctgaagga tgagcagcag ctagccaggc aaaggggca    60 atggcggctt cctgtgttct actgcacact gggcagaaga tgcctctgat tggtctgggt   120
acctggaaga gtgagcctgg tcaggtaaaa gcagctgtta agtatgccct tagcgtaggc   180
taccgccaca ttgattgtgc tgctatctac ggcaatgagc ctgagattgg ggaggccctg   240
aaggaggacg tgggaccagg caaggcggtg cctcgggagg agctgtttgt gacatccaag   300
ctgtggaaca ccaagcacca ccccgaggat gtggagcctg ccctccggaa gactctggct   360
gacctccagc tggagtatct ggacctgtac ctgatgcact ggccttatgc ctttgagcgg   420
ggagacaacc ccttccccaa gaatgctgat gggactatat gctacgactc cacccactac   480
aaggagactt ggaaggctct ggaggcactg gtggctaagg ggctggtgca ggcgctgggc   540
ctgtccaact tcaacagtcg gcagattgat gacatactca gtgtggcctc cgtgcgtcca   600
gctgtcttgc aggtggaatg ccacccatac ttggctcaaa atgagctaat tgcccactgc   660
caagcacgtg gcttggaggt aactgcttat agccctttgg gctcctctga tcgtgcatgg   720
cgtgatcctg atgagcctgt cctgctggag gaaccagtag tcctggcatt ggctgaaaag   780
tatggccgat ctccagctca gatcttgctc aggtggcagg tccagcggaa agtgatctgc   840
atccccaaaa gtatcactcc ttctcgaatc cttcagaaca tcaaggtgtt tgacttcacc   900
tttagcccag aagagatgaa gcagctaaat gccctgaaca aaaattggag atatattgtg   960
cctatgctta cggtggatgg gaagagagtc ccaagggatg cagggcatcc tctgtaccccc  1020 tttaatgacc cgtactgaga ccacagcttc ttggcctccc ttccagctct gcagctaatg  1080
aggtcctgcc acaacggaaa gagggagtta ataaagccat tggagcatcc at          1132
```

<210> SEQ ID NO 19
<211> LENGTH: 658
<212> TYPE: DNA
<213> ORGANISM: Human

<400> SEQUENCE: 19

```
accatgttta ttaagtgtta agcacagtgc ctggcacata acgtgctggg cggggtctat    60
ggtccagaca gggggaccag gcactttcca gcgcctggat ctgcagacgc gaggtcttct   120
gtattctggc caatcttggt gttgcagctg ctctctgggc ctcagtttgc ttgaactaaa   180
tgtaacgggg ccaacttagg tgaactttgg gaatccagcc aacctgactt tagggagagt   240
atggagccac ggatggcatt gtgaatccgg agggccgaca ccagaagaac ctgcaacgtg   300
gcatctgcta ccttacttcc cccggaaaag cgcctgcggc ggcgcctagg cgcgcggtgc   360
aatgtgggcc agcaaaaggc gaggctggcc ccgccccttg caccgccac gtggccagcg    420 ccacctgcct cattgtgccc aggagttctc caaacccgcg ctgcggagtg agtgaccaag   480
ttccggccag ttcgacctcg aggatccaga ggtggagacg gtactacctc ccagctctgt   540
tttccatccc cttcaggtcc ttcctcggga ggcggcgaag gcggtccacc ctgcgcgtga   600
tcctttatgc ccgccccctg cccctccctc cgggtggaac ttccccctca ccgctaga    658
```

<210> SEQ ID NO 20
<211> LENGTH: 502
<212> TYPE: DNA
<213> ORGANISM: Human

<400> SEQUENCE: 20

```
accatgttta ttaagtgtta agcacagtgc ctggcacata acgtgctggg cggggtctat    60
```

-continued

| | |
|---|---|
| ggtccagaca gggggaccag gcactttcca gcgcctggat ctgcagacgc gaggtcttct | 120 |
| gtattctggc caatcttggt gttgcagctg ctctctgggc ctcagtttgc ttgaactaaa | 180 |
| tgtaacgggg ccaacttagg tgaactttgg gaatccagcc aacctgactt tagggagagt | 240 |
| atggagccac ggatggcatt gtgaatccgg agggccgaca ccagaagaac ctgcaacgtg | 300 |
| gcatctgcta ccttacttcc cccggaaaag cgcctgcggc ggcgcctagg cgcgcggtgc | 360 |
| aatgtgggcc agcaaaaggc gaggctggcc ccgcccttg caccgcccac gtggccagcg | 420 |
| ccacctgcct cattgtgccc aggagttctc caaacccgcg ctgcggagtg agtgaccaag | 480 |
| ttccggccag ttcgacctcg ag | 502 |

<210> SEQ ID NO 21
<211> LENGTH: 157
<212> TYPE: DNA
<213> ORGANISM: Human

<400> SEQUENCE: 21

| | |
|---|---|
| ggatccagag gtggagacgg tactacctcc cagctctgtt ttccatcccc ttcaggtcct | 60 |
| tcctcgggag gcggcgaagg cggtccaccc tgcgcgtgat cctttatgcc cggcccctgc | 120 |
| ccctccctcc gggtggaact tccccctcac cgctaga | 157 |

<210> SEQ ID NO 22
<211> LENGTH: 445
<212> TYPE: DNA
<213> ORGANISM: Human

<400> SEQUENCE: 22

| | |
|---|---|
| accatgttta ttaagtgtta agcacagtgc ctggcacata acgtgctggg cggggtctat | 60 |
| ggtccagaca gggggaccag gcactttcca gcgcctggat ctgcagacgc gaggtcttct | 120 |
| gtattctggc caatcttggt gttgcagctg ctctctgggc ctcagtttgc ttgaactaaa | 180 |
| tgtaacgggg ccaacttagg tgaactttgg gaatccagcc aacctgactt tagggagagt | 240 |
| atggagccac ggatggcatt gtgaatccgg agggccgaca ccagaagaac ctgcaacgtg | 300 |
| gcatctgcta ccttacttcc cccggaaaag cgcctgcggc ggcgcctagg cgcgcggtgc | 360 |
| aatgtgggcc agcaaaaggc gaggctggcc ccgcccttg caccgcccac gtggccagcg | 420 |
| ccacctgcct cattgtgccc aggag | 445 |

<210> SEQ ID NO 23
<211> LENGTH: 296
<212> TYPE: DNA
<213> ORGANISM: Human

<400> SEQUENCE: 23

| | |
|---|---|
| gctctctggg cctcagtttg cttgaactaa atgtaacggg gccaacttag gtgaactttg | 60 |
| ggaatccagc caacctgact ttagggagag tatggagcca cggatggcat tgtgaatccg | 120 |
| gagggccgac accagaagaa cctgcaacgt ggcatctgct accttacttc ccccggaaaa | 180 |
| gcgcctgcgg cggcgcctag gcgcgcggtg caatgtgggc cagcaaaagg cgaggctggc | 240 |
| cccgcccctt gcaccgccca gtggccagc gccacctgcc tcattgtgcc caggag | 296 |

<210> SEQ ID NO 24
<211> LENGTH: 153
<212> TYPE: DNA
<213> ORGANISM: Human

<400> SEQUENCE: 24

```
gcaacgtggc atctgctacc ttacttcccc cggaaaagcg cctgcggcgg cgcctaggcg    60
cgcggtgcaa tgtgggccag caaaaggcga ggctggcccc gccccttgca ccgcccacgt   120
ggccagcgcc acctgcctca ttgtgcccag gag                                153

<210> SEQ ID NO 25
<211> LENGTH: 137
<212> TYPE: DNA
<213> ORGANISM: Human

<400> SEQUENCE: 25
taccttactt cccccggaaa agcgcctgcg gcggcgccta ggcgcgcggt gcaatgtggg    60
ccagcaaaag gcgaggctgg ccccgcccct gcaccgcccc acgtggccag cgccacctgc   120
ctcattgtgc ccaggag                                                  137

<210> SEQ ID NO 26
<211> LENGTH: 113
<212> TYPE: DNA
<213> ORGANISM: Human

<400> SEQUENCE: 26
cctgcggcgg cgcctaggcg cgcggtgcaa tgtgggccag caaaaggcga ggctggcccc    60
gccccttgca ccgcccacgt ggccagcgcc acctgcctca ttgtgcccag gag          113

<210> SEQ ID NO 27
<211> LENGTH: 95
<212> TYPE: DNA
<213> ORGANISM: Human

<400> SEQUENCE: 27
cgcgcggtgc aatgtgggcc agcaaaaggc gaggctggcc ccgcccttg caccgcccac     60 gtggccagcg ccacctgcct cattgtgccc aggag                               95

<210> SEQ ID NO 28
<211> LENGTH: 94
<212> TYPE: DNA
<213> ORGANISM: Human

<400> SEQUENCE: 28
gcgcggtgca atgtgggcca gcaaaaggcg aggctggccc cgcccttgc accgcccacg     60 tggccagcgc cacctgcctc attgtgccca ggag                                94

<210> SEQ ID NO 29
<211> LENGTH: 296
<212> TYPE: DNA
<213> ORGANISM: Human

<400> SEQUENCE: 29
ctcctgggca caatgaggca ggtggcgctg gccacgtggg cggtgcaagg ggcggggcca    60
gcctcgcctt ttgctggccc acattgcacc gcgcgcctag gcgccgccgc aggcgctttt   120 ccggggaag taaggtagca gatgccacgt tgcaggttct tctggtgtcg gccctccgga   180
ttcacaatgc catccgtggc tccatactct ccctaaagtc aggttggctg gattcccaaa   240
gttcacctaa gttggccccg ttacatttag ttcaagcaaa ctgaggccca gagagc       296

<210> SEQ ID NO 30
<211> LENGTH: 153
<212> TYPE: DNA
```

-continued

```
<213> ORGANISM: Human

<400> SEQUENCE: 30
ctcctgggca caatgaggca ggtggcgctg gccacgtggg cggtgcaagg ggcggggcca      60
gcctcgcctt ttgctggccc acattgcacc gcgcgcctag gcgccgccgc aggcgctttt    120
ccgggggaag taaggtagca gatgccacgt tgc                                 153

<210> SEQ ID NO 31
<211> LENGTH: 209
<212> TYPE: DNA
<213> ORGANISM: Human

<400> SEQUENCE: 31
gcaacgtggc atctgctacc ttacttcccc cggaaaagcg cctgcggcgg cgcctaggcg     60
cgcggtgcaa tgtgggccag caaaaggcga ggctggcccc gccccttgca ccgcccacgt    120
ggccagcgcc acctgcctca ttgtgcccag gagttctcca aacccgcgct gcggagtgag    180
tgaccaagtt ccggccagtt cgacctcga                                      209
```